US011541100B2

(12) United States Patent
Kweon et al.

(10) Patent No.: US 11,541,100 B2
(45) Date of Patent: Jan. 3, 2023

(54) PHARMACEUTICAL COMPOSITION COMPRISING NANOPERFORATOR FOR PREVENTING OR TREATING VIRAL INFECTIOUS DISEASES

(71) Applicant: MVRIX CO., LTD., Hwaseong-si (KR)

(72) Inventors: Dae-Hyuk Kweon, Suwon-si (KR); Byoungjae Kong, Suwon-si (KR); Woo-Jae Chung, Seoul (KR); Baik Lin Seong, Seoul (KR); Sukchan Lee, Suwon-si (KR)

(73) Assignee: MVRIX CO., LTD., Hwaseong-si (KR)

( * ) Notice: Subject to any disclaimer, the term of this patent is extended or adjusted under 35 U.S.C. 154(b) by 877 days.

(21) Appl. No.: 16/317,817

(22) PCT Filed: Jul. 14, 2017

(86) PCT No.: PCT/KR2017/007602

§ 371 (c)(1),
(2) Date: Jan. 14, 2019

(87) PCT Pub. No.: WO2018/012936

PCT Pub. Date: Jan. 18, 2018

(65) Prior Publication Data

US 2019/0255145 A1 Aug. 22, 2019

(30) Foreign Application Priority Data

Jul. 15, 2016 (KR) ........................ 10-2016-0090012
Jul. 14, 2017 (KR) ........................ 10-2017-0089655

(51) Int. Cl.

| | |
|---|---|
| ***A61P 31/12*** | (2006.01) |
| ***A61K 38/17*** | (2006.01) |
| ***A61K 39/12*** | (2006.01) |
| ***A61K 35/766*** | (2015.01) |
| ***A61K 35/763*** | (2015.01) |
| ***G01N 33/569*** | (2006.01) |
| ***A61K 9/00*** | (2006.01) |
| ***A61K 9/127*** | (2006.01) |
| ***G01N 33/566*** | (2006.01) |
| ***A61K 9/51*** | (2006.01) |

(52) U.S. Cl.

CPC ........ *A61K 38/1709* (2013.01); *A61K 9/0019* (2013.01); *A61K 9/0043* (2013.01); *A61K 9/0053* (2013.01); *A61K 9/127* (2013.01); *A61K 9/5123* (2013.01); *A61K 35/763* (2013.01); *A61K 35/766* (2013.01); *A61K 39/12* (2013.01); *A61P 31/12* (2018.01); *G01N 33/566* (2013.01); *G01N 33/569* (2013.01)

(58) Field of Classification Search

CPC ....... A61P 31/12; A61P 39/12; G01N 33/566; G01N 2405/04; A61K 9/1274; A61K 38/177; C12N 2760/16132; C12N 2710/16732

See application file for complete search history.

(56) References Cited

U.S. PATENT DOCUMENTS

2016/0089431 A1 3/2016 Bressi et al.

FOREIGN PATENT DOCUMENTS

| | | | |
|---|---|---|---|
| EP | 2058002 | A1 | 5/2009 |
| KR | 10-1334143 | B1 | 11/2013 |

OTHER PUBLICATIONS

Denisov et al. Directed Self-Assembly of Monodisperse Phospholipid Bilayer Nanodiscs With Controlled Size; Journal of the American Chemical Society, vol. 126, pp. 3477-3487. (Year: 2004).*

Matrosovich et al. Avian Influenza a Viruses Differ From Human Viruses By Recognition of Sialyloligosaccharides and Gangliosides and By a Higher Conservation of the Ha Receptor-Binding Site; Virology, vol. 233, pp. 224-234. (Year: 1997).*

Borch et al. Nanodisc-Based Co-Immunoprecipitation for Mass Spectrometric Identification of Membrane-Interacting Proteins; Molecular and Cellular Proteomics, vol. 10, No. 7, pp. 1-9. (Year: 2011).*

Numata et al. Nanodiscs as a Therapeutic Delivery Agent: Inhibition of Respiratory Syncytial Virus Infection in the Lung; International Journal of Nanomedicine, vol. 8, pp. 1417-1427. (Year: 2013).*

Nasr et al. Creating Large Covelently Circularized Nanodiscsand Their Application in Studying Viral Entry and Genome Translocation; Protein Science, vol. 24, Supplement 1, pp. 192-193. Abstract No. PI-028. (Year: 2015).*

Yelena V.Grinkova, et al., "Engineering extended membrane scaffold proteins for self-assembly of soluble nanoscale lipid bilayers"; Protein Engineering, Design & Selection; vol. 23 No. 11; pp. 843-848, 2010.

Saeui et al., "Ceil Surface and Membrane Engineering: Emerging Technologies and Applications", J. Funct. Biomater, 2015, vol. 6, pp. 454-485.

Galili et al."Inhalation of α-gal/sialic acid liposomes: a novel approach for inhibition of influenza virus infection?", Future Virol., 2016, vol. 11, No. 2, pp. 95-99.

(Continued)

*Primary Examiner* — Neil P Hammell
*Assistant Examiner* — Paul C Martin
(74) *Attorney, Agent, or Firm* — Sughrue Mion, PLLC

(57) ABSTRACT

The present invention relates to a nanoperforator having a lipid-bilayer nanodisc and a membrane-structured protein surrounding the nanodisc and to a pharmaceutical composition having the nanoperforator as an active ingredient for preventing or treating viral infectious diseases. The use of the lipid-bilayer nanoperforator provided in the present invention can lead to the safe prevention or treatment of a disease caused by viral infection regardless of whether the virus is a variant or not, and thus the present invention can be widely used for the safe and effective treatment of viral infectious diseases.

10 Claims, 19 Drawing Sheets

Specification includes a Sequence Listing.

(56) References Cited

OTHER PUBLICATIONS

Bhaitacharya et al., "Nanodisc-Incorporated Hemagglutinin Provides Protective Immunity against Influenza Virus Infection", 2010, vol. 84, No. 1, pp. 361-371.

International Search Report for Corresponding International Application No. PCT/KR2017/007602 (3 Pages) (dated Dec. 12, 2017).

* cited by examiner

[Fig. 1]
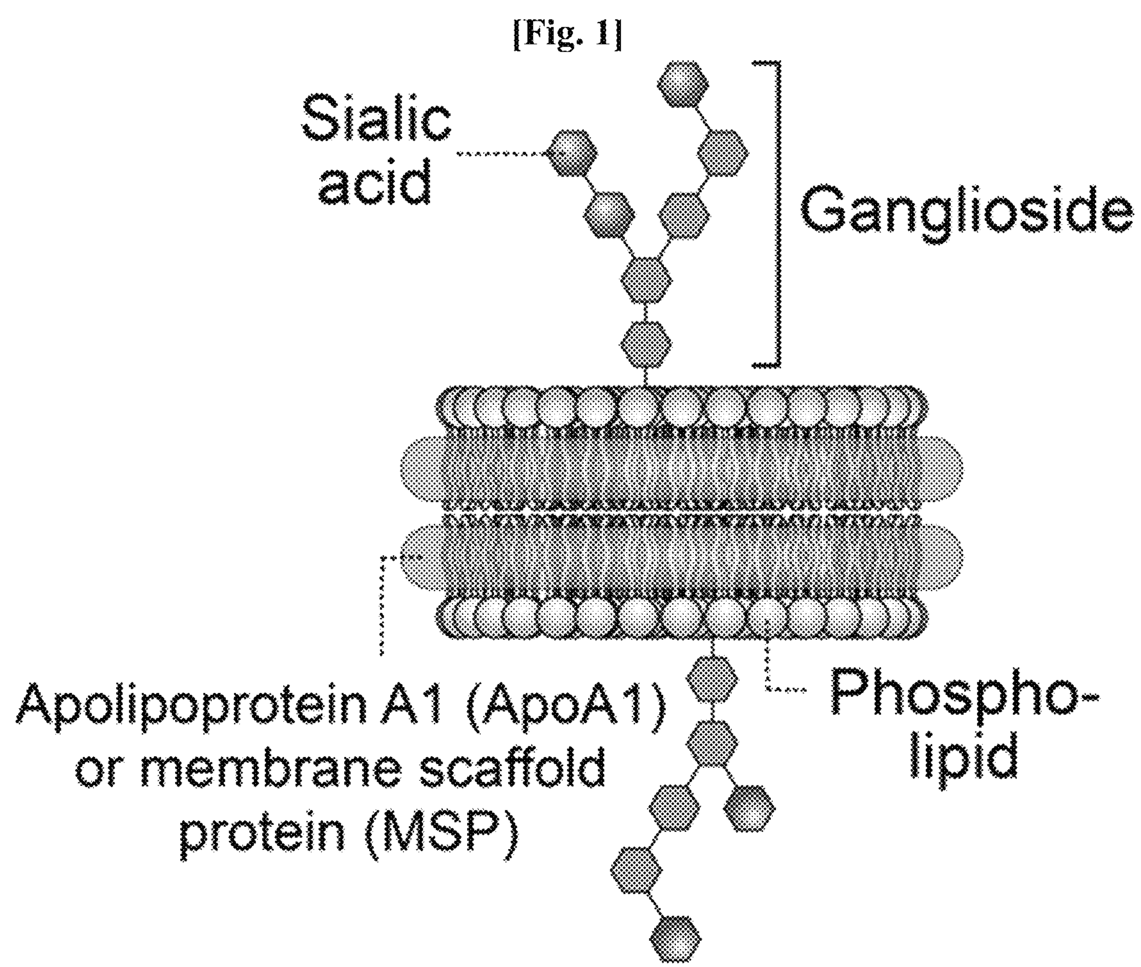

[Fig. 2A]
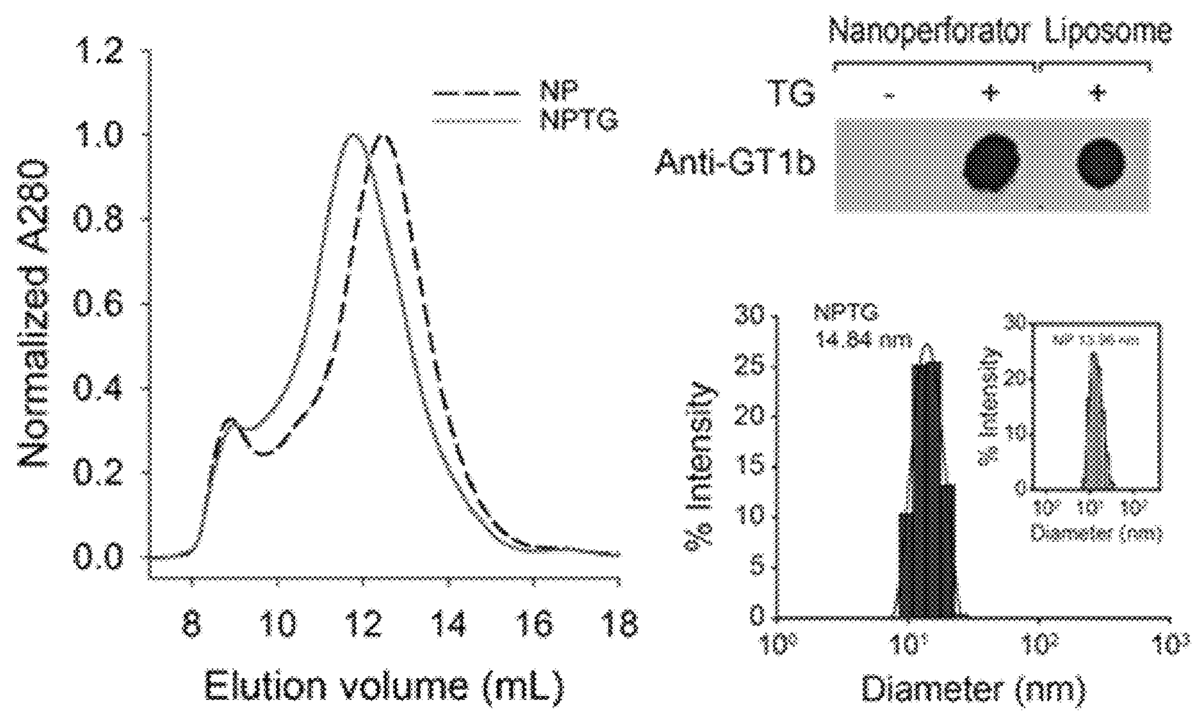
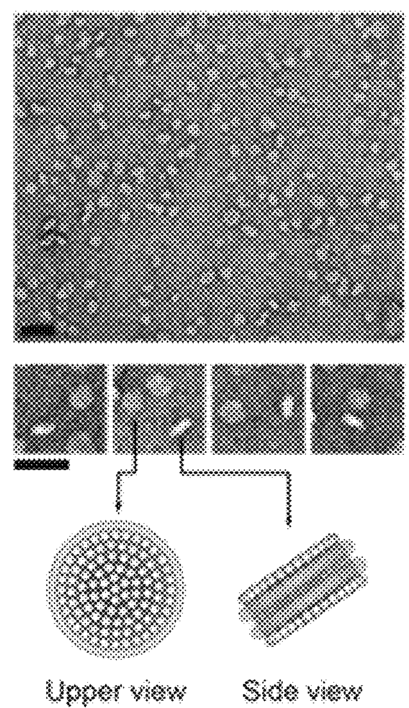

[Fig. 2B]
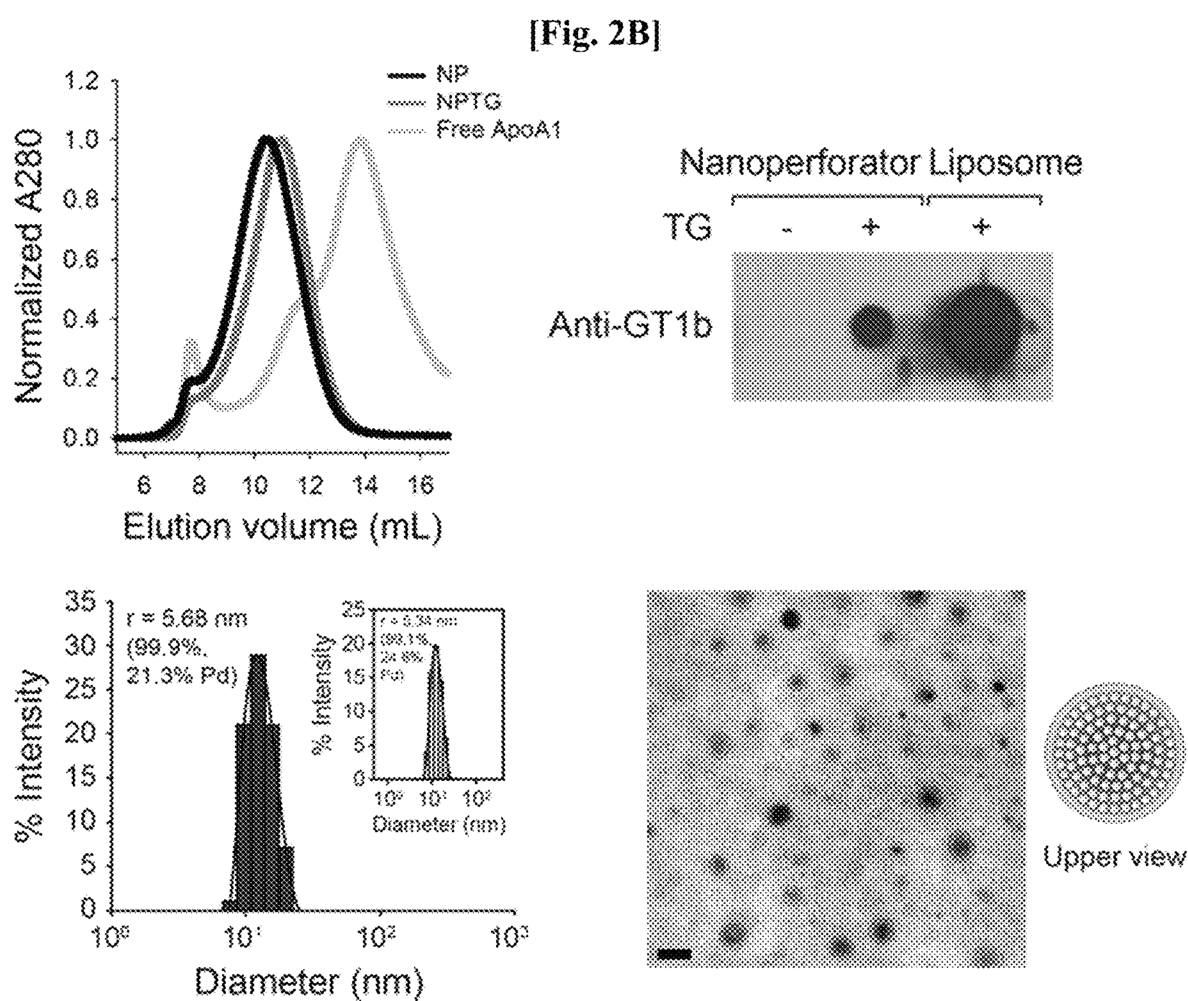

[Fig. 3]
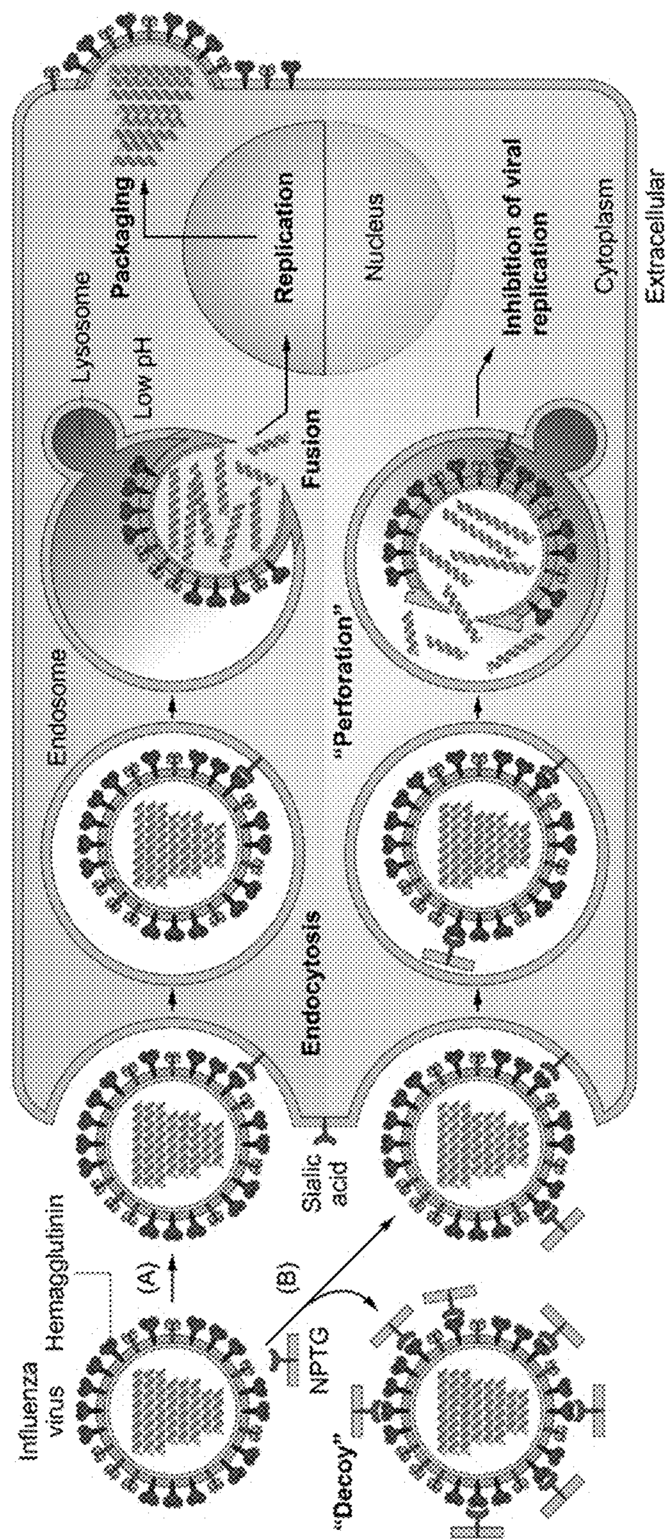

[Fig. 4]
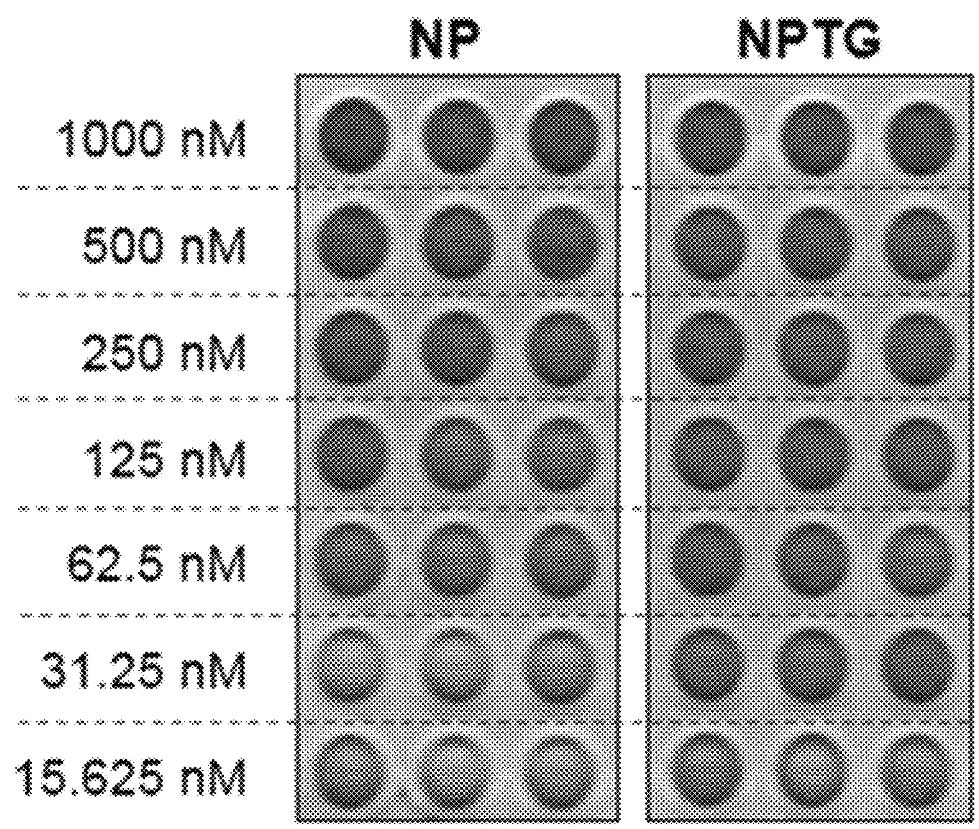
Cell only
(No virus infection
No sample treat)
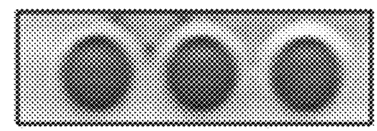
(-) control
(Virus infection
No sample treat)
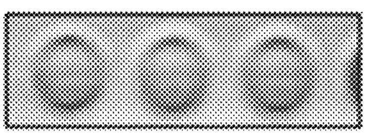
(+) control
(Virus infection
100 nM tamiflu)
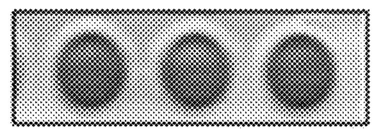
Cell line : MDCK
Virus strain : A/sydney/5/97(H3N2)

[Fig. 5A]
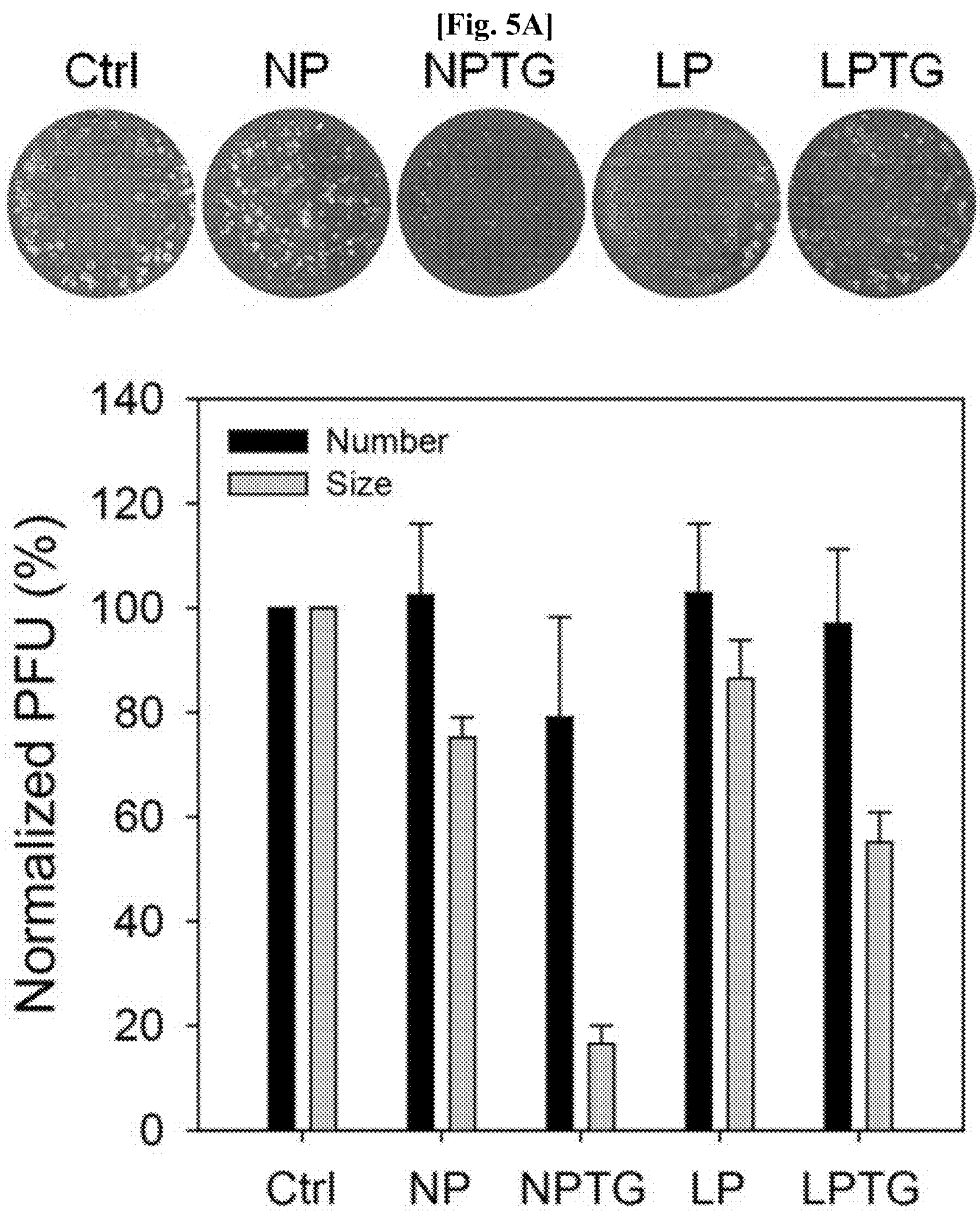

[Fig. 5B]
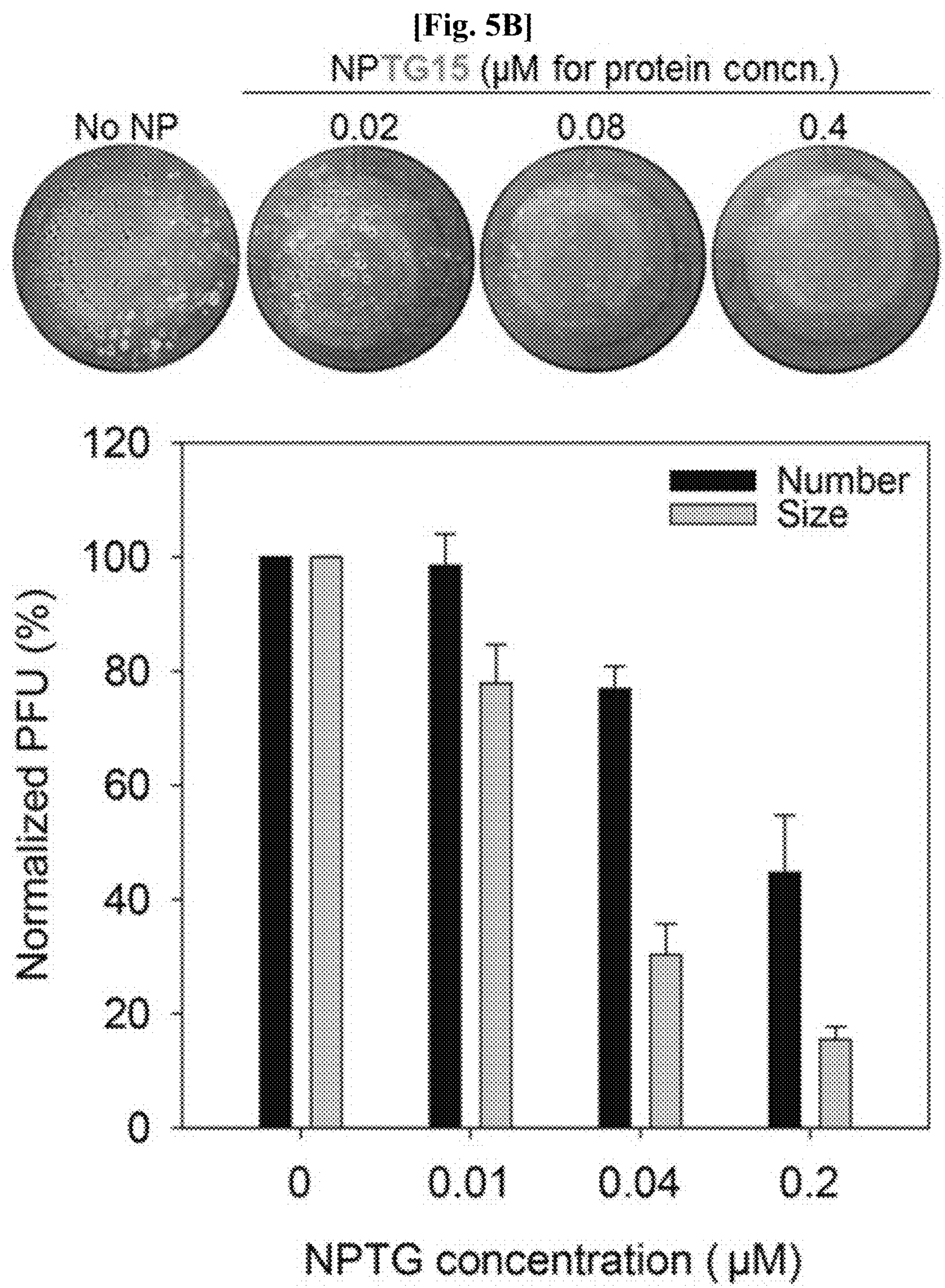

[Fig. 5C]
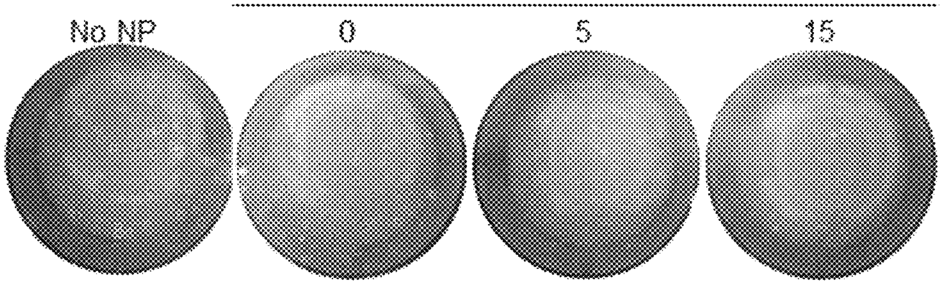
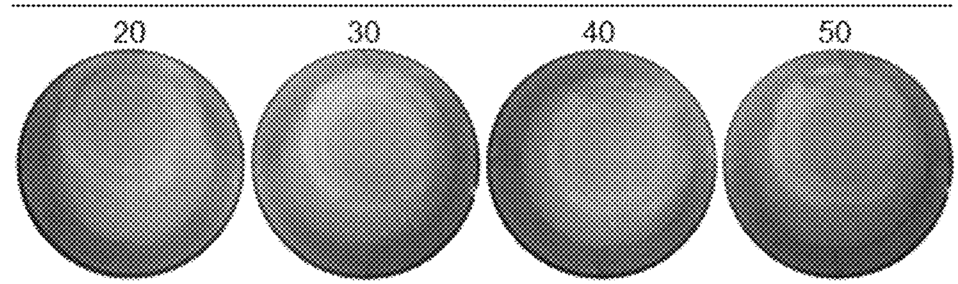
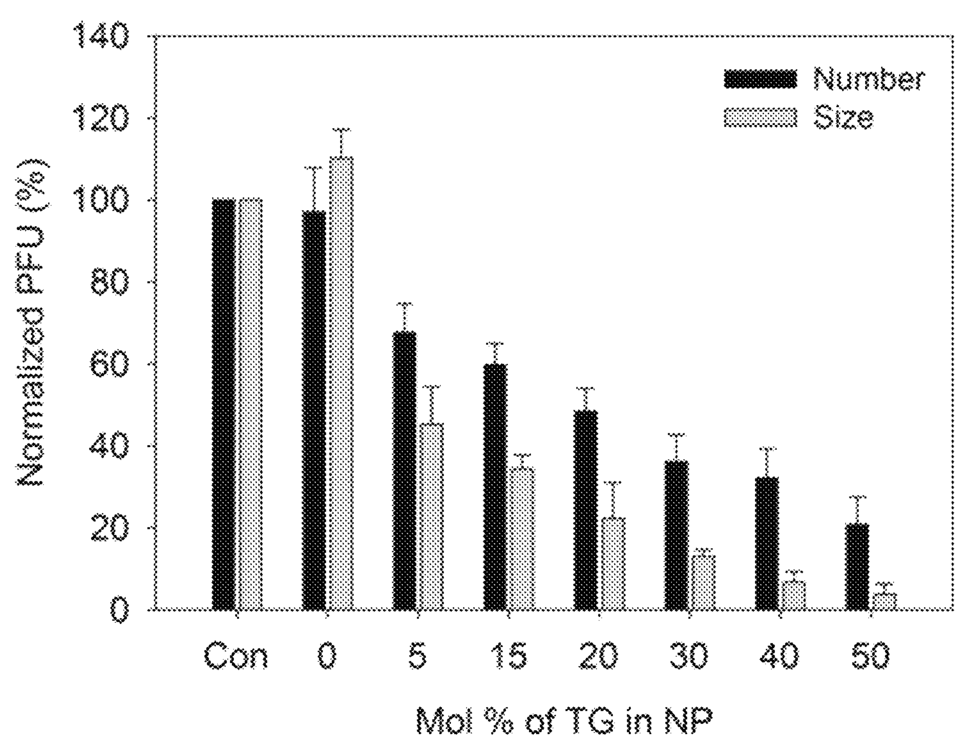

[Fig. 5D]
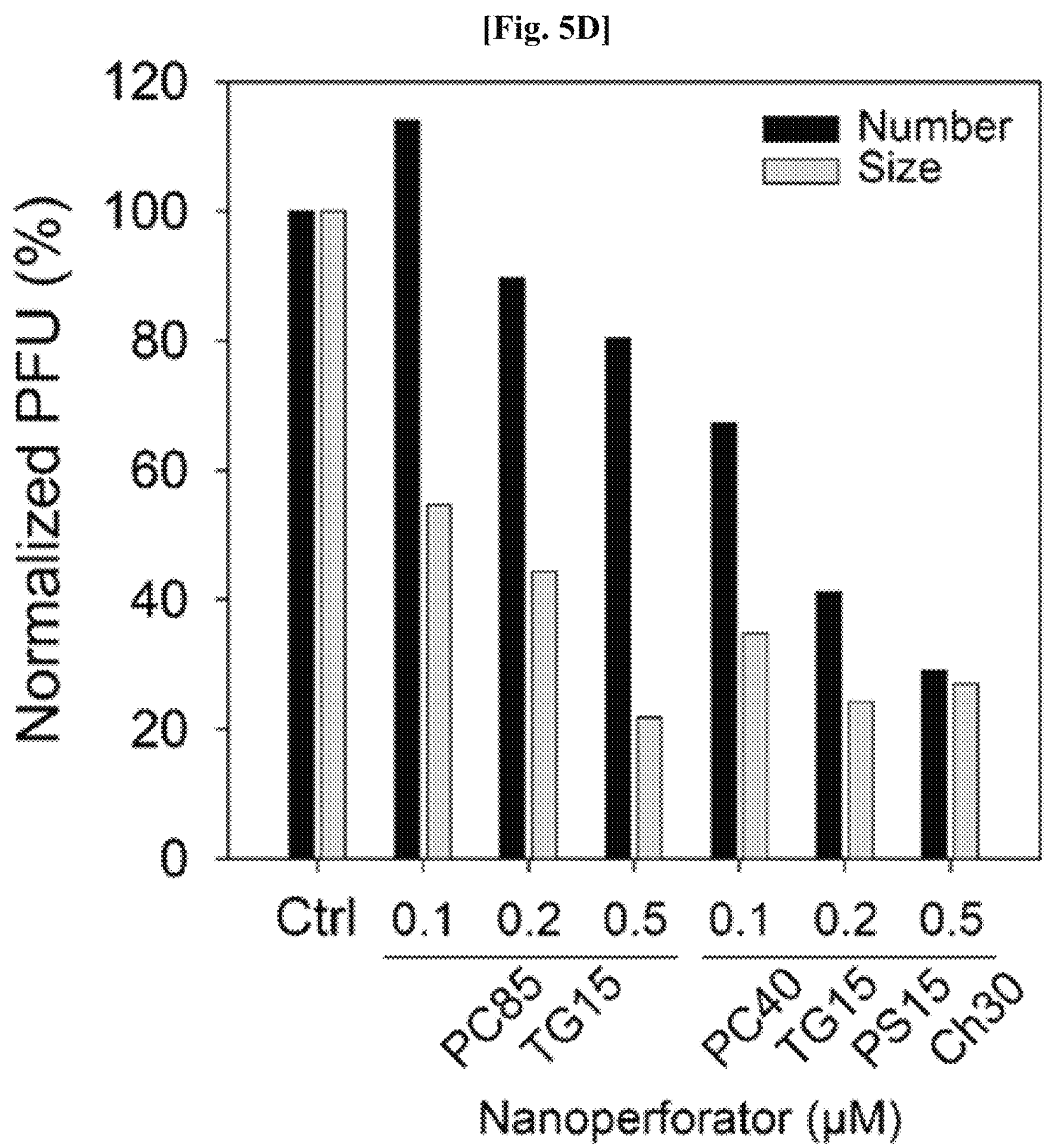

[Fig. 6]

Control H1N1 H1N1+NPTG

[Fig. 7]
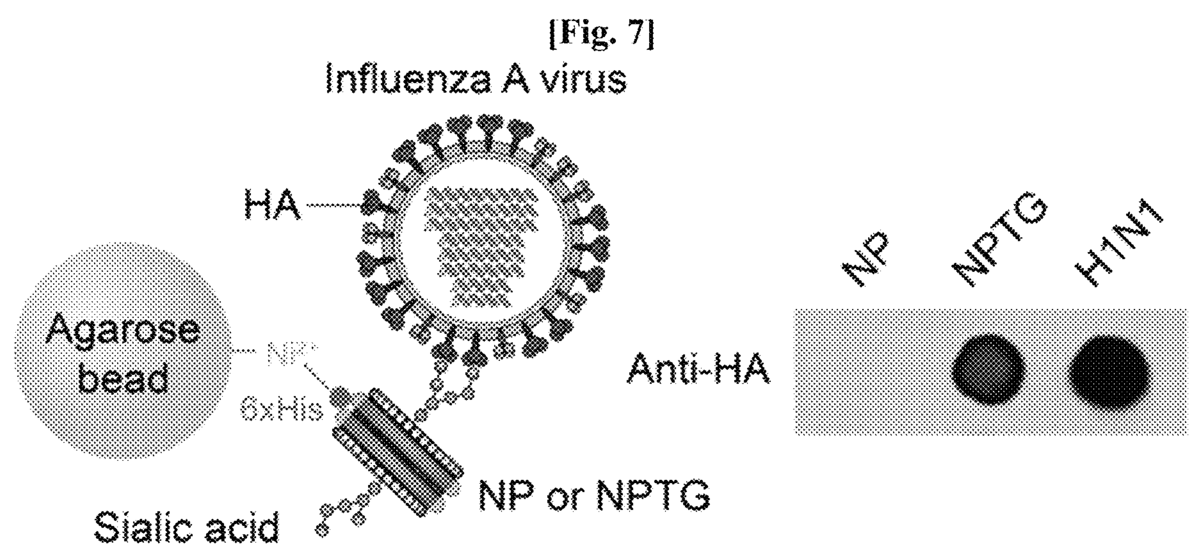

H1N1 + NPTG

[Fig. 9A]
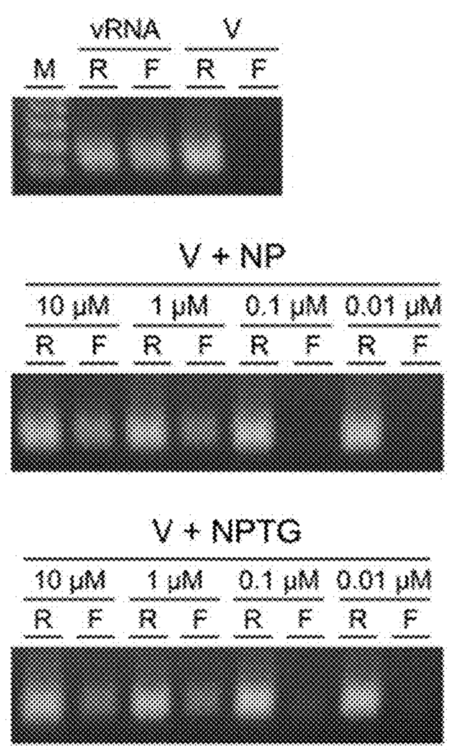
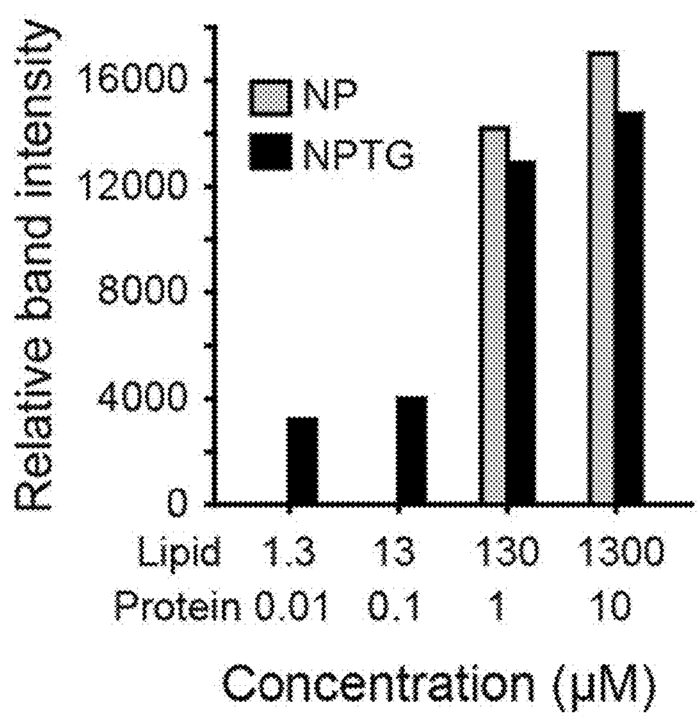

[Fig. 9B]
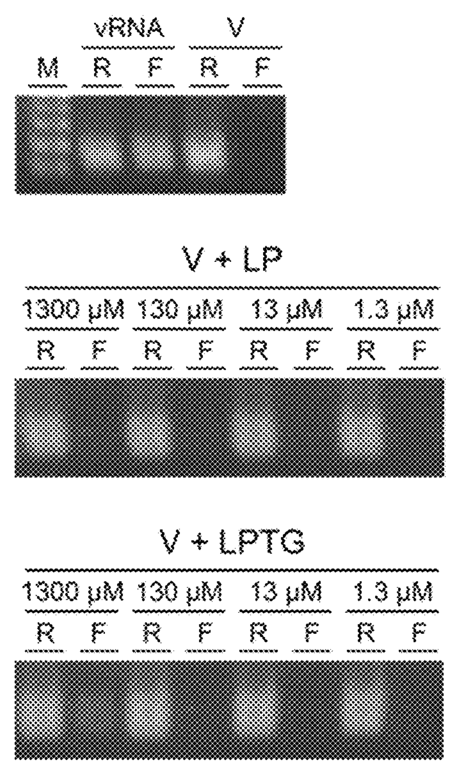
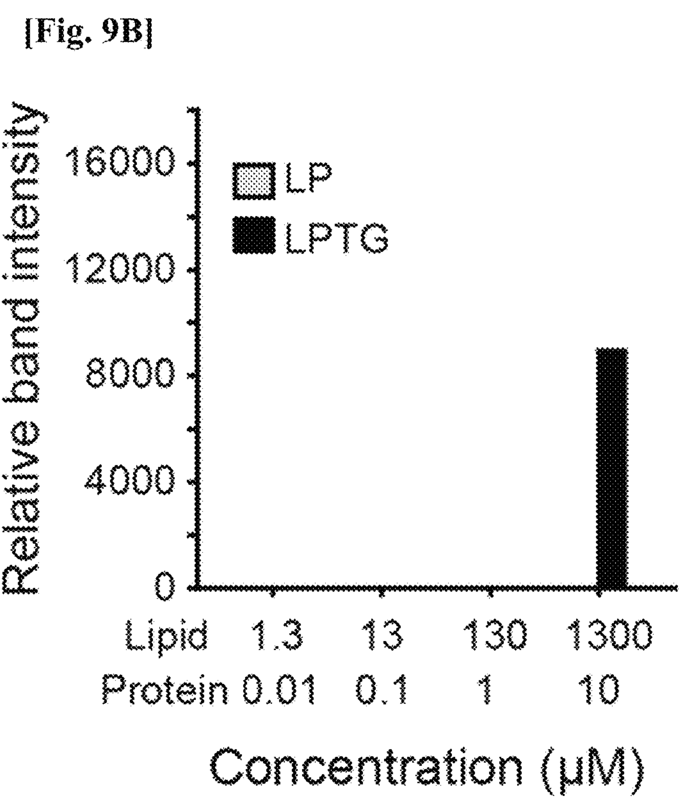

[Fig. 9C]
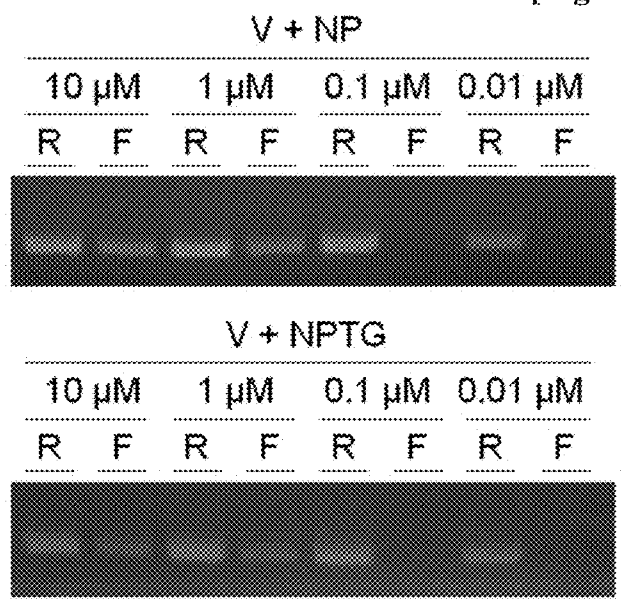
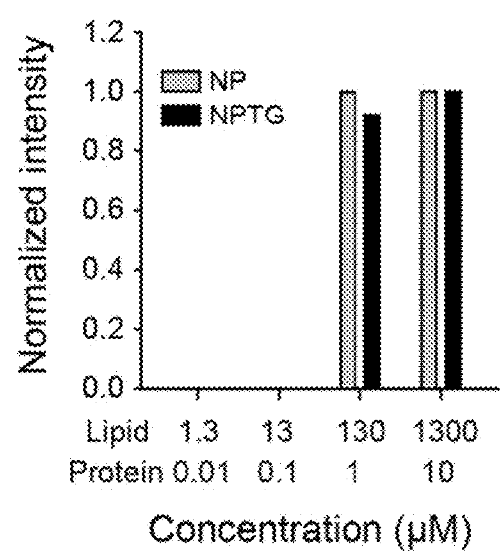

[Fig. 10]

[Fig. 11]
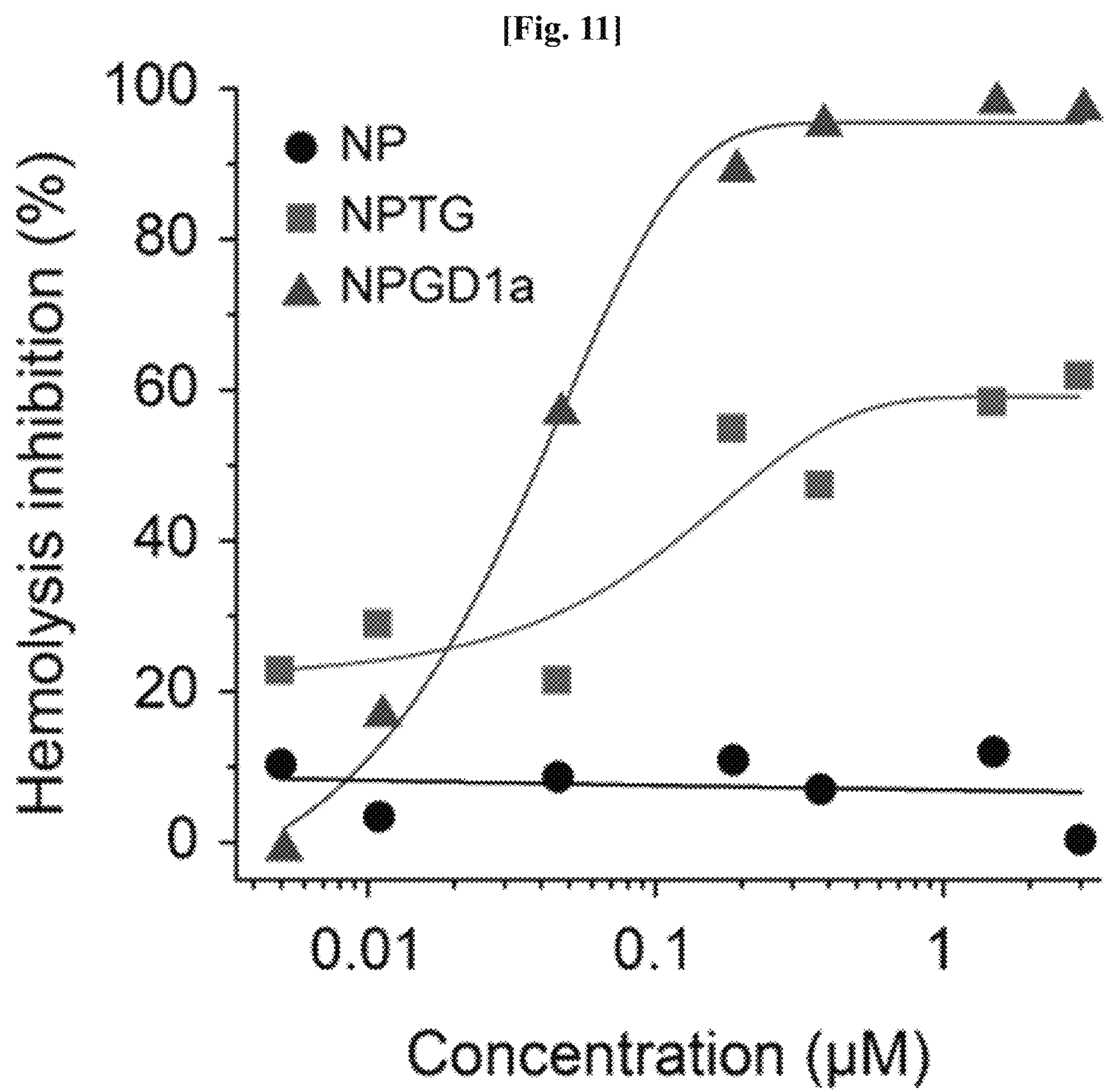

[Fig. 12]
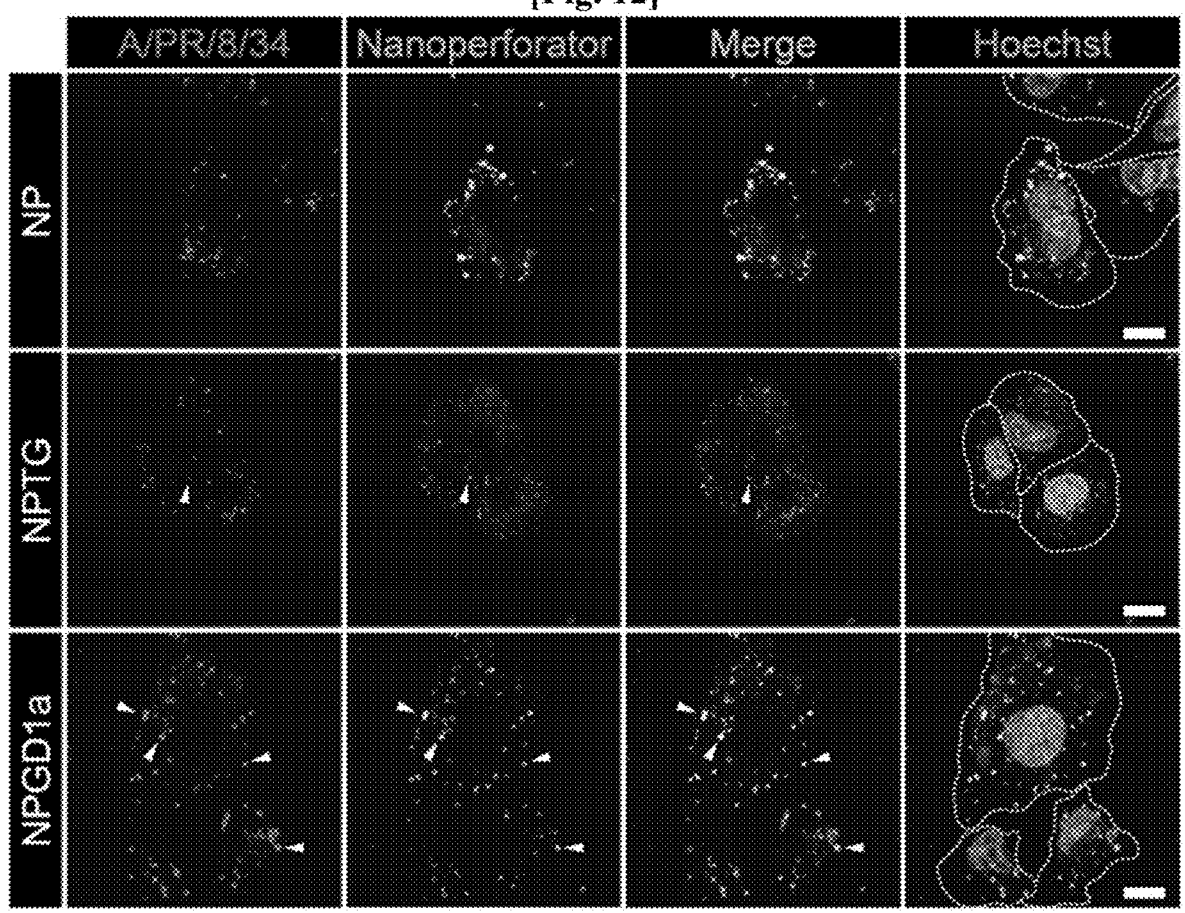

[Fig. 13]
Mock
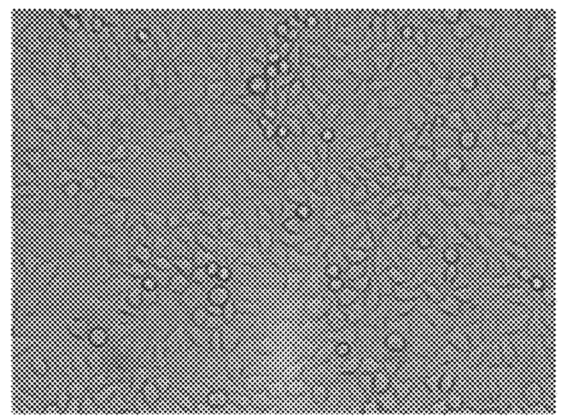
Positive
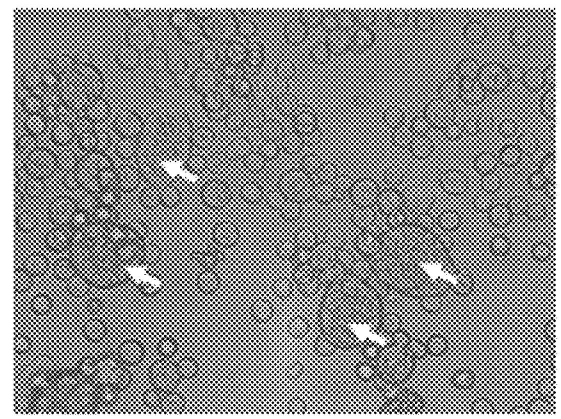
8 μM
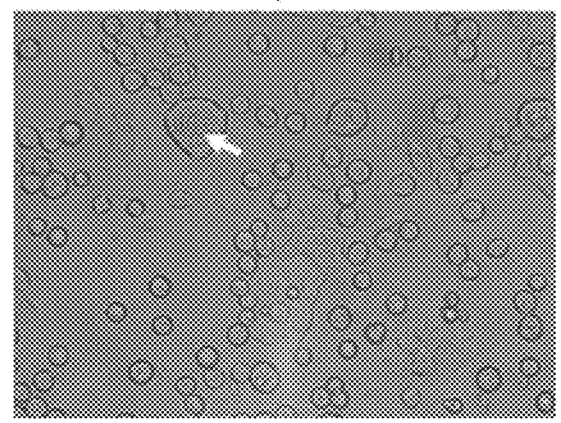
M.O.I = 1

SEQUENCE LISTING

```
<160> NUMBER OF SEQ ID NOS: 17

<210> SEQ ID NO 1
<211> LENGTH: 267
<212> TYPE: PRT
<213> ORGANISM: Artificial Sequence
<220> FEATURE:
<223> OTHER INFORMATION: ApoA-1

<400> SEQUENCE: 1

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220
```

```
Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265


<210> SEQ ID NO 2
<211> LENGTH: 100
<212> TYPE: PRT
<213> ORGANISM: Artificial Sequence
<220> FEATURE:
<223> OTHER INFORMATION: ApoA-2

<400> SEQUENCE: 2

Met Lys Leu Leu Ala Ala Thr Val Leu Leu Leu Thr Ile Cys Ser Leu
1               5                   10                  15

Glu Gly Ala Leu Val Arg Arg Gln Ala Lys Glu Pro Cys Val Glu Ser
            20                  25                  30

Leu Val Ser Gln Tyr Phe Gln Thr Val Thr Asp Tyr Gly Lys Asp Leu
        35                  40                  45

Met Glu Lys Val Lys Ser Pro Glu Leu Gln Ala Glu Ala Lys Ser Tyr
    50                  55                  60

Phe Glu Lys Ser Lys Glu Gln Leu Thr Pro Leu Ile Lys Lys Ala Gly
65                  70                  75                  80

Thr Glu Leu Val Asn Phe Leu Ser Tyr Phe Val Glu Leu Gly Thr Gln
                85                  90                  95

Pro Ala Thr Gln
            100


<210> SEQ ID NO 3
<211> LENGTH: 4563
<212> TYPE: PRT
<213> ORGANISM: Artificial Sequence
<220> FEATURE:
<223> OTHER INFORMATION: ApoB

<400> SEQUENCE: 3

Met Asp Pro Pro Arg Pro Ala Leu Leu Ala Leu Leu Ala Leu Pro Ala
1               5                   10                  15

Leu Leu Leu Leu Leu Leu Ala Gly Ala Arg Ala Glu Glu Glu Met Leu
            20                  25                  30

Glu Asn Val Ser Leu Val Cys Pro Lys Asp Ala Thr Arg Phe Lys His
        35                  40                  45

Leu Arg Lys Tyr Thr Tyr Asn Tyr Glu Ala Glu Ser Ser Ser Gly Val
    50                  55                  60

Pro Gly Thr Ala Asp Ser Arg Ser Ala Thr Arg Ile Asn Cys Lys Val
65                  70                  75                  80

Glu Leu Glu Val Pro Gln Leu Cys Ser Phe Ile Leu Lys Thr Ser Gln
                85                  90                  95

Cys Thr Leu Lys Glu Val Tyr Gly Phe Asn Pro Glu Gly Lys Ala Leu
            100                 105                 110

Leu Lys Lys Thr Lys Asn Ser Glu Glu Phe Ala Ala Ala Met Ser Arg
        115                 120                 125

Tyr Glu Leu Lys Leu Ala Ile Pro Glu Gly Lys Gln Val Phe Leu Tyr
    130                 135                 140

Pro Glu Lys Asp Glu Pro Thr Tyr Ile Leu Asn Ile Lys Arg Gly Ile
```

-continued

```
145                 150                 155                 160

Ile Ser Ala Leu Leu Val Pro Pro Glu Thr Glu Glu Ala Lys Gln Val
                165                 170                 175

Leu Phe Leu Asp Thr Val Tyr Gly Asn Cys Ser Thr His Phe Thr Val
            180                 185                 190

Lys Thr Arg Lys Gly Asn Val Ala Thr Glu Ile Ser Thr Glu Arg Asp
        195                 200                 205

Leu Gly Gln Cys Asp Arg Phe Lys Pro Ile Arg Thr Gly Ile Ser Pro
    210                 215                 220

Leu Ala Leu Ile Lys Gly Met Thr Arg Pro Leu Ser Thr Leu Ile Ser
225                 230                 235                 240

Ser Ser Gln Ser Cys Gln Tyr Thr Leu Asp Ala Lys Arg Lys His Val
                245                 250                 255

Ala Glu Ala Ile Cys Lys Glu Gln His Leu Phe Leu Pro Phe Ser Tyr
            260                 265                 270

Lys Asn Lys Tyr Gly Met Val Ala Gln Val Thr Gln Thr Leu Lys Leu
        275                 280                 285

Glu Asp Thr Pro Lys Ile Asn Ser Arg Phe Phe Gly Glu Gly Thr Lys
    290                 295                 300

Lys Met Gly Leu Ala Phe Glu Ser Thr Lys Ser Thr Ser Pro Pro Lys
305                 310                 315                 320

Gln Ala Glu Ala Val Leu Lys Thr Leu Gln Glu Leu Lys Lys Leu Thr
                325                 330                 335

Ile Ser Glu Gln Asn Ile Gln Arg Ala Asn Leu Phe Asn Lys Leu Val
            340                 345                 350

Thr Glu Leu Arg Gly Leu Ser Asp Glu Ala Val Thr Ser Leu Leu Pro
        355                 360                 365

Gln Leu Ile Glu Val Ser Ser Pro Ile Thr Leu Gln Ala Leu Val Gln
    370                 375                 380

Cys Gly Gln Pro Gln Cys Ser Thr His Ile Leu Gln Trp Leu Lys Arg
385                 390                 395                 400

Val His Ala Asn Pro Leu Leu Ile Asp Val Val Thr Tyr Leu Val Ala
                405                 410                 415

Leu Ile Pro Glu Pro Ser Ala Gln Gln Leu Arg Glu Ile Phe Asn Met
            420                 425                 430

Ala Arg Asp Gln Arg Ser Arg Ala Thr Leu Tyr Ala Leu Ser His Ala
        435                 440                 445

Val Asn Asn Tyr His Lys Thr Asn Pro Thr Gly Thr Gln Glu Leu Leu
    450                 455                 460

Asp Ile Ala Asn Tyr Leu Met Glu Gln Ile Gln Asp Asp Cys Thr Gly
465                 470                 475                 480

Asp Glu Asp Tyr Thr Tyr Leu Ile Leu Arg Val Ile Gly Asn Met Gly
                485                 490                 495

Gln Thr Met Glu Gln Leu Thr Pro Glu Leu Lys Ser Ser Ile Leu Lys
            500                 505                 510

Cys Val Gln Ser Thr Lys Pro Ser Leu Met Ile Gln Lys Ala Ala Ile
        515                 520                 525

Gln Ala Leu Arg Lys Met Glu Pro Lys Asp Lys Asp Gln Glu Val Leu
    530                 535                 540

Leu Gln Thr Phe Leu Asp Asp Ala Ser Pro Gly Asp Lys Arg Leu Ala
545                 550                 555                 560

Ala Tyr Leu Met Leu Met Arg Ser Pro Ser Gln Ala Asp Ile Asn Lys
                565                 570                 575
```

```
Ile Val Gln Ile Leu Pro Trp Glu Gln Asn Glu Gln Val Lys Asn Phe
            580                 585                 590

Val Ala Ser His Ile Ala Asn Ile Leu Asn Ser Glu Glu Leu Asp Ile
        595                 600                 605

Gln Asp Leu Lys Lys Leu Val Lys Glu Ala Leu Lys Glu Ser Gln Leu
    610                 615                 620

Pro Thr Val Met Asp Phe Arg Lys Phe Ser Arg Asn Tyr Gln Leu Tyr
625                 630                 635                 640

Lys Ser Val Ser Leu Pro Ser Leu Asp Pro Ala Ser Ala Lys Ile Glu
                645                 650                 655

Gly Asn Leu Ile Phe Asp Pro Asn Asn Tyr Leu Pro Lys Glu Ser Met
            660                 665                 670

Leu Lys Thr Thr Leu Thr Ala Phe Gly Phe Ala Ser Ala Asp Leu Ile
        675                 680                 685

Glu Ile Gly Leu Glu Gly Lys Gly Phe Glu Pro Thr Leu Glu Ala Leu
    690                 695                 700

Phe Gly Lys Gln Gly Phe Phe Pro Asp Ser Val Asn Lys Ala Leu Tyr
705                 710                 715                 720

Trp Val Asn Gly Gln Val Pro Asp Gly Val Ser Lys Val Leu Val Asp
                725                 730                 735

His Phe Gly Tyr Thr Lys Asp Asp Lys His Glu Gln Asp Met Val Asn
            740                 745                 750

Gly Ile Met Leu Ser Val Glu Lys Leu Ile Lys Asp Leu Lys Ser Lys
        755                 760                 765

Glu Val Pro Glu Ala Arg Ala Tyr Leu Arg Ile Leu Gly Glu Glu Leu
    770                 775                 780

Gly Phe Ala Ser Leu His Asp Leu Gln Leu Leu Gly Lys Leu Leu Leu
785                 790                 795                 800

Met Gly Ala Arg Thr Leu Gln Gly Ile Pro Gln Met Ile Gly Glu Val
                805                 810                 815

Ile Arg Lys Gly Ser Lys Asn Asp Phe Phe Leu His Tyr Ile Phe Met
            820                 825                 830

Glu Asn Ala Phe Glu Leu Pro Thr Gly Ala Gly Leu Gln Leu Gln Ile
        835                 840                 845

Ser Ser Ser Gly Val Ile Ala Pro Gly Ala Lys Ala Gly Val Lys Leu
    850                 855                 860

Glu Val Ala Asn Met Gln Ala Glu Leu Val Ala Lys Pro Ser Val Ser
865                 870                 875                 880

Val Glu Phe Val Thr Asn Met Gly Ile Ile Ile Pro Asp Phe Ala Arg
                885                 890                 895

Ser Gly Val Gln Met Asn Thr Asn Phe Phe His Glu Ser Gly Leu Glu
            900                 905                 910

Ala His Val Ala Leu Lys Ala Gly Lys Leu Lys Phe Ile Ile Pro Ser
        915                 920                 925

Pro Lys Arg Pro Val Lys Leu Leu Ser Gly Gly Asn Thr Leu His Leu
    930                 935                 940

Val Ser Thr Thr Lys Thr Glu Val Ile Pro Pro Leu Ile Glu Asn Arg
945                 950                 955                 960

Gln Ser Trp Ser Val Cys Lys Gln Val Phe Pro Gly Leu Asn Tyr Cys
                965                 970                 975

Thr Ser Gly Ala Tyr Ser Asn Ala Ser Ser Thr Asp Ser Ala Ser Tyr
            980                 985                 990
```

```
Tyr Pro Leu Thr Gly Asp Thr Arg Leu Glu Leu Glu Leu Arg Pro Thr
        995                1000                1005

Gly Glu Ile Glu Gln Tyr Ser Val Ser Ala Thr Tyr Glu Leu Gln Arg
    1010                1015                1020

Glu Asp Arg Ala Leu Val Asp Thr Leu Lys Phe Val Thr Gln Ala Glu
1025                1030                1035                1040

Gly Ala Lys Gln Thr Glu Ala Thr Met Thr Phe Lys Tyr Asn Arg Gln
                1045                1050                1055

Ser Met Thr Leu Ser Ser Glu Val Gln Ile Pro Asp Phe Asp Val Asp
            1060                1065                1070

Leu Gly Thr Ile Leu Arg Val Asn Asp Glu Ser Thr Glu Gly Lys Thr
        1075                1080                1085

Ser Tyr Arg Leu Thr Leu Asp Ile Gln Asn Lys Lys Ile Thr Glu Val
    1090                1095                1100

Ala Leu Met Gly His Leu Ser Cys Asp Thr Lys Glu Glu Arg Lys Ile
1105                1110                1115                1120

Lys Gly Val Ile Ser Ile Pro Arg Leu Gln Ala Glu Ala Arg Ser Glu
                1125                1130                1135

Ile Leu Ala His Trp Ser Pro Ala Lys Leu Leu Leu Gln Met Asp Ser
            1140                1145                1150

Ser Ala Thr Ala Tyr Gly Ser Thr Val Ser Lys Arg Val Ala Trp His
        1155                1160                1165

Tyr Asp Glu Glu Lys Ile Glu Phe Glu Trp Asn Thr Gly Thr Asn Val
    1170                1175                1180

Asp Thr Lys Lys Met Thr Ser Asn Phe Pro Val Asp Leu Ser Asp Tyr
1185                1190                1195                1200

Pro Lys Ser Leu His Met Tyr Ala Asn Arg Leu Leu Asp His Arg Val
                1205                1210                1215

Pro Gln Thr Asp Met Thr Phe Arg His Val Gly Ser Lys Leu Ile Val
            1220                1225                1230

Ala Met Ser Ser Trp Leu Gln Lys Ala Ser Gly Ser Leu Pro Tyr Thr
        1235                1240                1245

Gln Thr Leu Gln Asp His Leu Asn Ser Leu Lys Glu Phe Asn Leu Gln
    1250                1255                1260

Asn Met Gly Leu Pro Asp Phe His Ile Pro Glu Asn Leu Phe Leu Lys
1265                1270                1275                1280

Ser Asp Gly Arg Val Lys Tyr Thr Leu Asn Lys Asn Ser Leu Lys Ile
                1285                1290                1295

Glu Ile Pro Leu Pro Phe Gly Gly Lys Ser Ser Arg Asp Leu Lys Met
            1300                1305                1310

Leu Glu Thr Val Arg Thr Pro Ala Leu His Phe Lys Ser Val Gly Phe
        1315                1320                1325

His Leu Pro Ser Arg Glu Phe Gln Val Pro Thr Phe Thr Ile Pro Lys
    1330                1335                1340

Leu Tyr Gln Leu Gln Val Pro Leu Leu Gly Val Leu Asp Leu Ser Thr
1345                1350                1355                1360

Asn Val Tyr Ser Asn Leu Tyr Asn Trp Ser Ala Ser Tyr Ser Gly Gly
                1365                1370                1375

Asn Thr Ser Thr Asp His Phe Ser Leu Arg Ala Arg Tyr His Met Lys
            1380                1385                1390

Ala Asp Ser Val Val Asp Leu Leu Ser Tyr Asn Val Gln Gly Ser Gly
        1395                1400                1405

Glu Thr Thr Tyr Asp His Lys Asn Thr Phe Thr Leu Ser Cys Asp Gly
```

```
    1410                1415                1420

Ser Leu Arg His Lys Phe Leu Asp Ser Asn Ile Lys Phe Ser His Val
1425                1430                1435                1440

Glu Lys Leu Gly Asn Asn Pro Val Ser Lys Gly Leu Leu Ile Phe Asp
                1445                1450                1455

Ala Ser Ser Ser Trp Gly Pro Gln Met Ser Ala Ser Val His Leu Asp
            1460                1465                1470

Ser Lys Lys Lys Gln His Leu Phe Val Lys Glu Val Lys Ile Asp Gly
        1475                1480                1485

Gln Phe Arg Val Ser Ser Phe Tyr Ala Lys Gly Thr Tyr Gly Leu Ser
    1490                1495                1500

Cys Gln Arg Asp Pro Asn Thr Gly Arg Leu Asn Gly Glu Ser Asn Leu
1505                1510                1515                1520

Arg Phe Asn Ser Ser Tyr Leu Gln Gly Thr Asn Gln Ile Thr Gly Arg
                1525                1530                1535

Tyr Glu Asp Gly Thr Leu Ser Leu Thr Ser Thr Ser Asp Leu Gln Ser
            1540                1545                1550

Gly Ile Ile Lys Asn Thr Ala Ser Leu Lys Tyr Glu Asn Tyr Glu Leu
        1555                1560                1565

Thr Leu Lys Ser Asp Thr Asn Gly Lys Tyr Lys Asn Phe Ala Thr Ser
    1570                1575                1580

Asn Lys Met Asp Met Thr Phe Ser Lys Gln Asn Ala Leu Leu Arg Ser
1585                1590                1595                1600

Glu Tyr Gln Ala Asp Tyr Glu Ser Leu Arg Phe Phe Ser Leu Leu Ser
                1605                1610                1615

Gly Ser Leu Asn Ser His Gly Leu Glu Leu Asn Ala Asp Ile Leu Gly
            1620                1625                1630

Thr Asp Lys Ile Asn Ser Gly Ala His Lys Ala Thr Leu Arg Ile Gly
        1635                1640                1645

Gln Asp Gly Ile Ser Thr Ser Ala Thr Thr Asn Leu Lys Cys Ser Leu
    1650                1655                1660

Leu Val Leu Glu Asn Glu Leu Asn Ala Glu Leu Gly Leu Ser Gly Ala
1665                1670                1675                1680

Ser Met Lys Leu Thr Thr Asn Gly Arg Phe Arg Glu His Asn Ala Lys
                1685                1690                1695

Phe Ser Leu Asp Gly Lys Ala Ala Leu Thr Glu Leu Ser Leu Gly Ser
            1700                1705                1710

Ala Tyr Gln Ala Met Ile Leu Gly Val Asp Ser Lys Asn Ile Phe Asn
        1715                1720                1725

Phe Lys Val Ser Gln Glu Gly Leu Lys Leu Ser Asn Asp Met Met Gly
    1730                1735                1740

Ser Tyr Ala Glu Met Lys Phe Asp His Thr Asn Ser Leu Asn Ile Ala
1745                1750                1755                1760

Gly Leu Ser Leu Asp Phe Ser Ser Lys Leu Asp Asn Ile Tyr Ser Ser
                1765                1770                1775

Asp Lys Phe Tyr Lys Gln Thr Val Asn Leu Gln Leu Gln Pro Tyr Ser
            1780                1785                1790

Leu Val Thr Thr Leu Asn Ser Asp Leu Lys Tyr Asn Ala Leu Asp Leu
        1795                1800                1805

Thr Asn Asn Gly Lys Leu Arg Leu Glu Pro Leu Lys Leu His Val Ala
    1810                1815                1820

Gly Asn Leu Lys Gly Ala Tyr Gln Asn Asn Glu Ile Lys His Ile Tyr
1825                1830                1835                1840
```

```
Ala Ile Ser Ser Ala Ala Leu Ser Ala Ser Tyr Lys Ala Asp Thr Val
                1845                1850                1855

Ala Lys Val Gln Gly Val Glu Phe Ser His Arg Leu Asn Thr Asp Ile
            1860                1865                1870

Ala Gly Leu Ala Ser Ala Ile Asp Met Ser Thr Asn Tyr Asn Ser Asp
        1875                1880                1885

Ser Leu His Phe Ser Asn Val Phe Arg Ser Val Met Ala Pro Phe Thr
    1890                1895                1900

Met Thr Ile Asp Ala His Thr Asn Gly Asn Gly Lys Leu Ala Leu Trp
1905                1910                1915                1920

Gly Glu His Thr Gly Gln Leu Tyr Ser Lys Phe Leu Leu Lys Ala Glu
                1925                1930                1935

Pro Leu Ala Phe Thr Phe Ser His Asp Tyr Lys Gly Ser Thr Ser His
            1940                1945                1950

His Leu Val Ser Arg Lys Ser Ile Ser Ala Ala Leu Glu His Lys Val
        1955                1960                1965

Ser Ala Leu Leu Thr Pro Ala Glu Gln Thr Gly Thr Trp Lys Leu Lys
    1970                1975                1980

Thr Gln Phe Asn Asn Asn Glu Tyr Ser Gln Asp Leu Asp Ala Tyr Asn
1985                1990                1995                2000

Thr Lys Asp Lys Ile Gly Val Glu Leu Thr Gly Arg Thr Leu Ala Asp
                2005                2010                2015

Leu Thr Leu Leu Asp Ser Pro Ile Lys Val Pro Leu Leu Leu Ser Glu
            2020                2025                2030

Pro Ile Asn Ile Ile Asp Ala Leu Glu Met Arg Asp Ala Val Glu Lys
        2035                2040                2045

Pro Gln Glu Phe Thr Ile Val Ala Phe Val Lys Tyr Asp Lys Asn Gln
    2050                2055                2060

Asp Val His Ser Ile Asn Leu Pro Phe Phe Glu Thr Leu Gln Glu Tyr
2065                2070                2075                2080

Phe Glu Arg Asn Arg Gln Thr Ile Ile Val Val Leu Glu Asn Val Gln
                2085                2090                2095

Arg Asn Leu Lys His Ile Asn Ile Asp Gln Phe Val Arg Lys Tyr Arg
            2100                2105                2110

Ala Ala Leu Gly Lys Leu Pro Gln Gln Ala Asn Asp Tyr Leu Asn Ser
        2115                2120                2125

Phe Asn Trp Glu Arg Gln Val Ser His Ala Lys Glu Lys Leu Thr Ala
    2130                2135                2140

Leu Thr Lys Lys Tyr Arg Ile Thr Glu Asn Asp Ile Gln Ile Ala Leu
2145                2150                2155                2160

Asp Asp Ala Lys Ile Asn Phe Asn Glu Lys Leu Ser Gln Leu Gln Thr
                2165                2170                2175

Tyr Met Ile Gln Phe Asp Gln Tyr Ile Lys Asp Ser Tyr Asp Leu His
            2180                2185                2190

Asp Leu Lys Ile Ala Ile Ala Asn Ile Ile Asp Glu Ile Ile Glu Lys
        2195                2200                2205

Leu Lys Ser Leu Asp Glu His Tyr His Ile Arg Val Asn Leu Val Lys
    2210                2215                2220

Thr Ile His Asp Leu His Leu Phe Ile Glu Asn Ile Asp Phe Asn Lys
2225                2230                2235                2240

Ser Gly Ser Ser Thr Ala Ser Trp Ile Gln Asn Val Asp Thr Lys Tyr
                2245                2250                2255
```

```
Gln Ile Arg Ile Gln Ile Gln Glu Lys Leu Gln Gln Leu Lys Arg His
            2260                2265                2270

Ile Gln Asn Ile Asp Ile Gln His Leu Ala Gly Lys Leu Lys Gln His
        2275                2280                2285

Ile Glu Ala Ile Asp Val Arg Val Leu Leu Asp Gln Leu Gly Thr Thr
    2290                2295                2300

Ile Ser Phe Glu Arg Ile Asn Asp Val Leu Glu His Val Lys His Phe
2305                2310                2315                2320

Val Ile Asn Leu Ile Gly Asp Phe Glu Val Ala Glu Lys Ile Asn Ala
                2325                2330                2335

Phe Arg Ala Lys Val His Glu Leu Ile Glu Arg Tyr Glu Val Asp Gln
            2340                2345                2350

Gln Ile Gln Val Leu Met Asp Lys Leu Val Glu Leu Ala His Gln Tyr
        2355                2360                2365

Lys Leu Lys Glu Thr Ile Gln Lys Leu Ser Asn Val Leu Gln Gln Val
    2370                2375                2380

Lys Ile Lys Asp Tyr Phe Glu Lys Leu Val Gly Phe Ile Asp Asp Ala
2385                2390                2395                2400

Val Lys Lys Leu Asn Glu Leu Ser Phe Lys Thr Phe Ile Glu Asp Val
                2405                2410                2415

Asn Lys Phe Leu Asp Met Leu Ile Lys Lys Leu Lys Ser Phe Asp Tyr
            2420                2425                2430

His Gln Phe Val Asp Glu Thr Asn Asp Lys Ile Arg Glu Val Thr Gln
        2435                2440                2445

Arg Leu Asn Gly Glu Ile Gln Ala Leu Glu Leu Pro Gln Lys Ala Glu
    2450                2455                2460

Ala Leu Lys Leu Phe Leu Glu Glu Thr Lys Ala Thr Val Ala Val Tyr
2465                2470                2475                2480

Leu Glu Ser Leu Gln Asp Thr Lys Ile Thr Leu Ile Ile Asn Trp Leu
                2485                2490                2495

Gln Glu Ala Leu Ser Ser Ala Ser Leu Ala His Met Lys Ala Lys Phe
            2500                2505                2510

Arg Glu Thr Leu Glu Asp Thr Arg Asp Arg Met Tyr Gln Met Asp Ile
        2515                2520                2525

Gln Gln Glu Leu Gln Arg Tyr Leu Ser Leu Val Gly Gln Val Tyr Ser
    2530                2535                2540

Thr Leu Val Thr Tyr Ile Ser Asp Trp Trp Thr Leu Ala Ala Lys Asn
2545                2550                2555                2560

Leu Thr Asp Phe Ala Glu Gln Tyr Ser Ile Gln Asp Trp Ala Lys Arg
                2565                2570                2575

Met Lys Ala Leu Val Glu Gln Gly Phe Thr Val Pro Glu Ile Lys Thr
            2580                2585                2590

Ile Leu Gly Thr Met Pro Ala Phe Glu Val Ser Leu Gln Ala Leu Gln
        2595                2600                2605

Lys Ala Thr Phe Gln Thr Pro Asp Phe Ile Val Pro Leu Thr Asp Leu
    2610                2615                2620

Arg Ile Pro Ser Val Gln Ile Asn Phe Lys Asp Leu Lys Asn Ile Lys
2625                2630                2635                2640

Ile Pro Ser Arg Phe Ser Thr Pro Glu Phe Thr Ile Leu Asn Thr Phe
                2645                2650                2655

His Ile Pro Ser Phe Thr Ile Asp Phe Val Glu Met Lys Val Lys Ile
            2660                2665                2670

Ile Arg Thr Ile Asp Gln Met Leu Asn Ser Glu Leu Gln Trp Pro Val
```

```
        2675                2680                2685

Pro Asp Ile Tyr Leu Arg Asp Leu Lys Val Glu Asp Ile Pro Leu Ala
    2690                2695                2700

Arg Ile Thr Leu Pro Asp Phe Arg Leu Pro Glu Ile Ala Ile Pro Glu
2705                2710                2715                2720

Phe Ile Ile Pro Thr Leu Asn Leu Asn Asp Phe Gln Val Pro Asp Leu
                2725                2730                2735

His Ile Pro Glu Phe Gln Leu Pro His Ile Ser His Thr Ile Glu Val
            2740                2745                2750

Pro Thr Phe Gly Lys Leu Tyr Ser Ile Leu Lys Ile Gln Ser Pro Leu
        2755                2760                2765

Phe Thr Leu Asp Ala Asn Ala Asp Ile Gly Asn Gly Thr Thr Ser Ala
    2770                2775                2780

Asn Glu Ala Gly Ile Ala Ala Ser Ile Thr Ala Lys Gly Glu Ser Lys
2785                2790                2795                2800

Leu Glu Val Leu Asn Phe Asp Phe Gln Ala Asn Ala Gln Leu Ser Asn
                2805                2810                2815

Pro Lys Ile Asn Pro Leu Ala Leu Lys Glu Ser Val Lys Phe Ser Ser
            2820                2825                2830

Lys Tyr Leu Arg Thr Glu His Gly Ser Glu Met Leu Phe Phe Gly Asn
        2835                2840                2845

Ala Ile Glu Gly Lys Ser Asn Thr Val Ala Ser Leu His Thr Glu Lys
    2850                2855                2860

Asn Thr Leu Glu Leu Ser Asn Gly Val Ile Val Lys Ile Asn Asn Gln
2865                2870                2875                2880

Leu Thr Leu Asp Ser Asn Thr Lys Tyr Phe His Lys Leu Asn Ile Pro
                2885                2890                2895

Lys Leu Asp Phe Ser Ser Gln Ala Asp Leu Arg Asn Glu Ile Lys Thr
            2900                2905                2910

Leu Leu Lys Ala Gly His Ile Ala Trp Thr Ser Ser Gly Lys Gly Ser
        2915                2920                2925

Trp Lys Trp Ala Cys Pro Arg Phe Ser Asp Glu Gly Thr His Glu Ser
    2930                2935                2940

Gln Ile Ser Phe Thr Ile Glu Gly Pro Leu Thr Ser Phe Gly Leu Ser
2945                2950                2955                2960

Asn Lys Ile Asn Ser Lys His Leu Arg Val Asn Gln Asn Leu Val Tyr
                2965                2970                2975

Glu Ser Gly Ser Leu Asn Phe Ser Lys Leu Glu Ile Gln Ser Gln Val
            2980                2985                2990

Asp Ser Gln His Val Gly His Ser Val Leu Thr Ala Lys Gly Met Ala
        2995                3000                3005

Leu Phe Gly Glu Gly Lys Ala Glu Phe Thr Gly Arg His Asp Ala His
    3010                3015                3020

Leu Asn Gly Lys Val Ile Gly Thr Leu Lys Asn Ser Leu Phe Phe Ser
3025                3030                3035                3040

Ala Gln Pro Phe Glu Ile Thr Ala Ser Thr Asn Asn Glu Gly Asn Leu
                3045                3050                3055

Lys Val Arg Phe Pro Leu Arg Leu Thr Gly Lys Ile Asp Phe Leu Asn
            3060                3065                3070

Asn Tyr Ala Leu Phe Leu Ser Pro Ser Ala Gln Gln Ala Ser Trp Gln
        3075                3080                3085

Val Ser Ala Arg Phe Asn Gln Tyr Lys Tyr Asn Gln Asn Phe Ser Ala
    3090                3095                3100
```

```
Gly Asn Asn Glu Asn Ile Met Glu Ala His Val Gly Ile Asn Gly Glu
3105                3110                3115                3120

Ala Asn Leu Asp Phe Leu Asn Ile Pro Leu Thr Ile Pro Glu Met Arg
                3125                3130                3135

Leu Pro Tyr Thr Ile Ile Thr Thr Pro Pro Leu Lys Asp Phe Ser Leu
            3140                3145                3150

Trp Glu Lys Thr Gly Leu Lys Glu Phe Leu Lys Thr Thr Lys Gln Ser
        3155                3160                3165

Phe Asp Leu Ser Val Lys Ala Gln Tyr Lys Lys Asn Lys His Arg His
    3170                3175                3180

Ser Ile Thr Asn Pro Leu Ala Val Leu Cys Glu Phe Ile Ser Gln Ser
3185                3190                3195                3200

Ile Lys Ser Phe Asp Arg His Phe Glu Lys Asn Arg Asn Asn Ala Leu
                3205                3210                3215

Asp Phe Val Thr Lys Ser Tyr Asn Glu Thr Lys Ile Lys Phe Asp Lys
            3220                3225                3230

Tyr Lys Ala Glu Lys Ser His Asp Glu Leu Pro Arg Thr Phe Gln Ile
        3235                3240                3245

Pro Gly Tyr Thr Val Pro Val Val Asn Val Glu Val Ser Pro Phe Thr
    3250                3255                3260

Ile Glu Met Ser Ala Phe Gly Tyr Val Phe Pro Lys Ala Val Ser Met
3265                3270                3275                3280

Pro Ser Phe Ser Ile Leu Gly Ser Asp Val Arg Val Pro Ser Tyr Thr
                3285                3290                3295

Leu Ile Leu Pro Ser Leu Glu Leu Pro Val Leu His Val Pro Arg Asn
            3300                3305                3310

Leu Lys Leu Ser Leu Pro Asp Phe Lys Glu Leu Cys Thr Ile Ser His
        3315                3320                3325

Ile Phe Ile Pro Ala Met Gly Asn Ile Thr Tyr Asp Phe Ser Phe Lys
    3330                3335                3340

Ser Ser Val Ile Thr Leu Asn Thr Asn Ala Glu Leu Phe Asn Gln Ser
3345                3350                3355                3360

Asp Ile Val Ala His Leu Leu Ser Ser Ser Ser Ser Val Ile Asp Ala
                3365                3370                3375

Leu Gln Tyr Lys Leu Glu Gly Thr Thr Arg Leu Thr Arg Lys Arg Gly
            3380                3385                3390

Leu Lys Leu Ala Thr Ala Leu Ser Leu Ser Asn Lys Phe Val Glu Gly
        3395                3400                3405

Ser His Asn Ser Thr Val Ser Leu Thr Thr Lys Asn Met Glu Val Ser
    3410                3415                3420

Val Ala Thr Thr Thr Lys Ala Gln Ile Pro Ile Leu Arg Met Asn Phe
3425                3430                3435                3440

Lys Gln Glu Leu Asn Gly Asn Thr Lys Ser Lys Pro Thr Val Ser Ser
                3445                3450                3455

Ser Met Glu Phe Lys Tyr Asp Phe Asn Ser Ser Met Leu Tyr Ser Thr
            3460                3465                3470

Ala Lys Gly Ala Val Asp His Lys Leu Ser Leu Glu Ser Leu Thr Ser
        3475                3480                3485

Tyr Phe Ser Ile Glu Ser Ser Thr Lys Gly Asp Val Lys Gly Ser Val
    3490                3495                3500

Leu Ser Arg Glu Tyr Ser Gly Thr Ile Ala Ser Glu Ala Asn Thr Tyr
3505                3510                3515                3520
```

```
Leu Asn Ser Lys Ser Thr Arg Ser Ser Val Lys Leu Gln Gly Thr Ser
                3525                3530                3535

Lys Ile Asp Asp Ile Trp Asn Leu Glu Val Lys Glu Asn Phe Ala Gly
            3540                3545                3550

Glu Ala Thr Leu Gln Arg Ile Tyr Ser Leu Trp Glu His Ser Thr Lys
        3555                3560                3565

Asn His Leu Gln Leu Glu Gly Leu Phe Phe Thr Asn Gly Glu His Thr
    3570                3575                3580

Ser Lys Ala Thr Leu Glu Leu Ser Pro Trp Gln Met Ser Ala Leu Val
3585                3590                3595                3600

Gln Val His Ala Ser Gln Pro Ser Ser Phe His Asp Phe Pro Asp Leu
                3605                3610                3615

Gly Gln Glu Val Ala Leu Asn Ala Asn Thr Lys Asn Gln Lys Ile Arg
            3620                3625                3630

Trp Lys Asn Glu Val Arg Ile His Ser Gly Ser Phe Gln Ser Gln Val
        3635                3640                3645

Glu Leu Ser Asn Asp Gln Glu Lys Ala His Leu Asp Ile Ala Gly Ser
    3650                3655                3660

Leu Glu Gly His Leu Arg Phe Leu Lys Asn Ile Ile Leu Pro Val Tyr
3665                3670                3675                3680

Asp Lys Ser Leu Trp Asp Phe Leu Lys Leu Asp Val Thr Thr Ser Ile
                3685                3690                3695

Gly Arg Arg Gln His Leu Arg Val Ser Thr Ala Phe Val Tyr Thr Lys
            3700                3705                3710

Asn Pro Asn Gly Tyr Ser Phe Ser Ile Pro Val Lys Val Leu Ala Asp
        3715                3720                3725

Lys Phe Ile Ile Pro Gly Leu Lys Leu Asn Asp Leu Asn Ser Val Leu
    3730                3735                3740

Val Met Pro Thr Phe His Val Pro Phe Thr Asp Leu Gln Val Pro Ser
3745                3750                3755                3760

Cys Lys Leu Asp Phe Arg Glu Ile Gln Ile Tyr Lys Lys Leu Arg Thr
                3765                3770                3775

Ser Ser Phe Ala Leu Asn Leu Pro Thr Leu Pro Glu Val Lys Phe Pro
            3780                3785                3790

Glu Val Asp Val Leu Thr Lys Tyr Ser Gln Pro Glu Asp Ser Leu Ile
        3795                3800                3805

Pro Phe Phe Glu Ile Thr Val Pro Glu Ser Gln Leu Thr Val Ser Gln
    3810                3815                3820

Phe Thr Leu Pro Lys Ser Val Ser Asp Gly Ile Ala Ala Leu Asp Leu
3825                3830                3835                3840

Asn Ala Val Ala Asn Lys Ile Ala Asp Phe Glu Leu Pro Thr Ile Ile
                3845                3850                3855

Val Pro Glu Gln Thr Ile Glu Ile Pro Ser Ile Lys Phe Ser Val Pro
            3860                3865                3870

Ala Gly Ile Val Ile Pro Ser Phe Gln Ala Leu Thr Ala Arg Phe Glu
        3875                3880                3885

Val Asp Ser Pro Val Tyr Asn Ala Thr Trp Ser Ala Ser Leu Lys Asn
    3890                3895                3900

Lys Ala Asp Tyr Val Glu Thr Val Leu Asp Ser Thr Cys Ser Ser Thr
3905                3910                3915                3920

Val Gln Phe Leu Glu Tyr Glu Leu Asn Val Leu Gly Thr His Lys Ile
                3925                3930                3935

Glu Asp Gly Thr Leu Ala Ser Lys Thr Lys Gly Thr Phe Ala His Arg
```

```
            3940                3945                3950

Asp Phe Ser Ala Glu Tyr Glu Glu Asp Gly Lys Tyr Glu Gly Leu Gln
        3955                3960                3965

Glu Trp Glu Gly Lys Ala His Leu Asn Ile Lys Ser Pro Ala Phe Thr
    3970                3975                3980

Asp Leu His Leu Arg Tyr Gln Lys Asp Lys Lys Gly Ile Ser Thr Ser
3985                3990                3995                4000

Ala Ala Ser Pro Ala Val Gly Thr Val Gly Met Asp Met Asp Glu Asp
                4005                4010                4015

Asp Asp Phe Ser Lys Trp Asn Phe Tyr Tyr Ser Pro Gln Ser Ser Pro
            4020                4025                4030

Asp Lys Lys Leu Thr Ile Phe Lys Thr Glu Leu Arg Val Arg Glu Ser
        4035                4040                4045

Asp Glu Glu Thr Gln Ile Lys Val Asn Trp Glu Glu Glu Ala Ala Ser
    4050                4055                4060

Gly Leu Leu Thr Ser Leu Lys Asp Asn Val Pro Lys Ala Thr Gly Val
4065                4070                4075                4080

Leu Tyr Asp Tyr Val Asn Lys Tyr His Trp Glu His Thr Gly Leu Thr
                4085                4090                4095

Leu Arg Glu Val Ser Ser Lys Leu Arg Arg Asn Leu Gln Asn Asn Ala
            4100                4105                4110

Glu Trp Val Tyr Gln Gly Ala Ile Arg Gln Ile Asp Asp Ile Asp Val
        4115                4120                4125

Arg Phe Gln Lys Ala Ala Ser Gly Thr Thr Gly Thr Tyr Gln Glu Trp
    4130                4135                4140

Lys Asp Lys Ala Gln Asn Leu Tyr Gln Glu Leu Leu Thr Gln Glu Gly
4145                4150                4155                4160

Gln Ala Ser Phe Gln Gly Leu Lys Asp Asn Val Phe Asp Gly Leu Val
                4165                4170                4175

Arg Val Thr Gln Glu Phe His Met Lys Val Lys His Leu Ile Asp Ser
            4180                4185                4190

Leu Ile Asp Phe Leu Asn Phe Pro Arg Phe Gln Phe Pro Gly Lys Pro
        4195                4200                4205

Gly Ile Tyr Thr Arg Glu Glu Leu Cys Thr Met Phe Ile Arg Glu Val
    4210                4215                4220

Gly Thr Val Leu Ser Gln Val Tyr Ser Lys Val His Asn Gly Ser Glu
4225                4230                4235                4240

Ile Leu Phe Ser Tyr Phe Gln Asp Leu Val Ile Thr Leu Pro Phe Glu
                4245                4250                4255

Leu Arg Lys His Lys Leu Ile Asp Val Ile Ser Met Tyr Arg Glu Leu
            4260                4265                4270

Leu Lys Asp Leu Ser Lys Glu Ala Gln Glu Val Phe Lys Ala Ile Gln
        4275                4280                4285

Ser Leu Lys Thr Thr Glu Val Leu Arg Asn Leu Gln Asp Leu Leu Gln
    4290                4295                4300

Phe Ile Phe Gln Leu Ile Glu Asp Asn Ile Lys Gln Leu Lys Glu Met
4305                4310                4315                4320

Lys Phe Thr Tyr Leu Ile Asn Tyr Ile Gln Asp Glu Ile Asn Thr Ile
                4325                4330                4335

Phe Ser Asp Tyr Ile Pro Tyr Val Phe Lys Leu Leu Lys Glu Asn Leu
            4340                4345                4350

Cys Leu Asn Leu His Lys Phe Asn Glu Phe Ile Gln Asn Glu Leu Gln
        4355                4360                4365
```

```
Glu Ala Ser Gln Glu Leu Gln Gln Ile His Gln Tyr Ile Met Ala Leu
    4370                4375                4380

Arg Glu Glu Tyr Phe Asp Pro Ser Ile Val Gly Trp Thr Val Lys Tyr
4385                4390                4395                4400

Tyr Glu Leu Glu Glu Lys Ile Val Ser Leu Ile Lys Asn Leu Leu Val
                4405                4410                4415

Ala Leu Lys Asp Phe His Ser Glu Tyr Ile Val Ser Ala Ser Asn Phe
            4420                4425                4430

Thr Ser Gln Leu Ser Ser Gln Val Glu Gln Phe Leu His Arg Asn Ile
        4435                4440                4445

Gln Glu Tyr Leu Ser Ile Leu Thr Asp Pro Asp Gly Lys Gly Lys Glu
    4450                4455                4460

Lys Ile Ala Glu Leu Ser Ala Thr Ala Gln Glu Ile Ile Lys Ser Gln
4465                4470                4475                4480

Ala Ile Ala Thr Lys Lys Ile Ile Ser Asp Tyr His Gln Gln Phe Arg
                4485                4490                4495

Tyr Lys Leu Gln Asp Phe Ser Asp Gln Leu Ser Asp Tyr Tyr Glu Lys
            4500                4505                4510

Phe Ile Ala Glu Ser Lys Arg Leu Ile Asp Leu Ser Ile Gln Asn Tyr
        4515                4520                4525

His Thr Phe Leu Ile Tyr Ile Thr Glu Leu Leu Lys Lys Leu Gln Ser
    4530                4535                4540

Thr Thr Val Met Asn Pro Tyr Met Lys Leu Ala Pro Gly Glu Leu Thr
4545                4550                4555                4560

Ile Ile Leu


<210> SEQ ID NO 4
<211> LENGTH: 83
<212> TYPE: PRT
<213> ORGANISM: Artificial Sequence
<220> FEATURE:
<223> OTHER INFORMATION: ApoC1

<400> SEQUENCE: 4

Met Arg Leu Phe Leu Ser Leu Pro Val Leu Val Val Val Leu Ser Ile
1               5                   10                  15

Val Leu Glu Gly Pro Ala Pro Ala Gln Gly Thr Pro Asp Val Ser Ser
            20                  25                  30

Ala Leu Asp Lys Leu Lys Glu Phe Gly Asn Thr Leu Glu Asp Lys Ala
        35                  40                  45

Arg Glu Leu Ile Ser Arg Ile Lys Gln Ser Glu Leu Ser Ala Lys Met
    50                  55                  60

Arg Glu Trp Phe Ser Glu Thr Phe Gln Lys Val Lys Glu Lys Leu Lys
65                  70                  75                  80

Ile Asp Ser


<210> SEQ ID NO 5
<211> LENGTH: 99
<212> TYPE: PRT
<213> ORGANISM: Artificial Sequence
<220> FEATURE:
<223> OTHER INFORMATION: ApoC3

<400> SEQUENCE: 5

Met Gln Pro Arg Val Leu Leu Val Val Ala Leu Leu Ala Leu Leu Ala
1               5                   10                  15
```

```
Ser Ala Arg Ala Ser Glu Ala Glu Asp Ala Ser Leu Leu Ser Phe Met
            20                  25                  30

Gln Gly Tyr Met Lys His Ala Thr Lys Thr Ala Lys Asp Ala Leu Ser
        35                  40                  45

Ser Val Gln Glu Ser Gln Val Ala Gln Gln Ala Arg Gly Trp Val Thr
    50                  55                  60

Asp Gly Phe Ser Ser Leu Lys Asp Tyr Trp Ser Thr Val Lys Asp Lys
65                  70                  75                  80

Phe Ser Glu Phe Trp Asp Leu Asp Pro Glu Val Arg Pro Thr Ser Ala
                85                  90                  95

Val Ala Ala


<210> SEQ ID NO 6
<211> LENGTH: 212
<212> TYPE: PRT
<213> ORGANISM: Artificial Sequence
<220> FEATURE:
<223> OTHER INFORMATION: MSP1

<400> SEQUENCE: 6

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln
    210


<210> SEQ ID NO 7
<211> LENGTH: 212
<212> TYPE: PRT
<213> ORGANISM: Artificial Sequence
<220> FEATURE:
<223> OTHER INFORMATION: MSP1D1

<400> SEQUENCE: 7
```

```
Met Gly His His His His His His His Asp Tyr Asp Ile Pro Thr Thr
1               5                   10                  15

Glu Asn Leu Tyr Phe Gln Gly Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln
    210
```

```
<210> SEQ ID NO 8
<211> LENGTH: 201
<212> TYPE: PRT
<213> ORGANISM: Artificial Sequence
<220> FEATURE:
<223> OTHER INFORMATION: MSP1D2

<400> SEQUENCE: 8

Met Gly His His His His His His His Asp Tyr Asp Ile Pro Thr Thr
1               5                   10                  15

Glu Asn Leu Tyr Phe Gln Gly Pro Val Thr Gln Glu Phe Trp Asp Asn
            20                  25                  30

Leu Glu Lys Glu Thr Glu Gly Leu Arg Gln Glu Met Ser Lys Asp Leu
        35                  40                  45

Glu Glu Val Lys Ala Lys Val Gln Pro Tyr Leu Asp Asp Phe Gln Lys
    50                  55                  60

Lys Trp Gln Glu Glu Met Glu Leu Tyr Arg Gln Lys Val Glu Pro Leu
65                  70                  75                  80

Arg Ala Glu Leu Gln Glu Gly Ala Arg Gln Lys Leu His Glu Leu Gln
                85                  90                  95

Glu Lys Leu Ser Pro Leu Gly Glu Glu Met Arg Asp Arg Ala Arg Ala
            100                 105                 110

His Val Asp Ala Leu Arg Thr His Leu Ala Pro Tyr Ser Asp Glu Leu
        115                 120                 125

Arg Gln Arg Leu Ala Ala Arg Leu Glu Ala Leu Lys Glu Asn Gly Gly
    130                 135                 140
```

```
Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
                165                 170                 175

Leu Pro Val Leu Glu Ser Phe Lys Val Ser Phe Leu Ser Ala Leu Glu
            180                 185                 190

Glu Tyr Thr Lys Lys Leu Asn Thr Gln
        195                 200


<210> SEQ ID NO 9
<211> LENGTH: 234
<212> TYPE: PRT
<213> ORGANISM: Artificial Sequence
<220> FEATURE:
<223> OTHER INFORMATION: MSP1E1

<400> SEQUENCE: 9

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Tyr Leu Asp Asp Phe Gln
                85                  90                  95

Lys Lys Trp Gln Glu Glu Met Glu Leu Tyr Arg Gln Lys Val Glu Pro
            100                 105                 110

Leu Arg Ala Glu Leu Gln Glu Gly Ala Arg Gln Lys Leu His Glu Leu
        115                 120                 125

Gln Glu Lys Leu Ser Pro Leu Gly Glu Glu Met Arg Asp Arg Ala Arg
    130                 135                 140

Ala His Val Asp Ala Leu Arg Thr His Leu Ala Pro Tyr Ser Asp Glu
145                 150                 155                 160

Leu Arg Gln Arg Leu Ala Ala Arg Leu Glu Ala Leu Lys Glu Asn Gly
                165                 170                 175

Gly Ala Arg Leu Ala Glu Tyr His Ala Lys Ala Thr Glu His Leu Ser
            180                 185                 190

Thr Leu Ser Glu Lys Ala Lys Pro Ala Leu Glu Asp Leu Arg Gln Gly
        195                 200                 205

Leu Leu Pro Val Leu Glu Ser Phe Lys Val Ser Phe Leu Ser Ala Leu
    210                 215                 220

Glu Glu Tyr Thr Lys Lys Leu Asn Thr Gln
225                 230


<210> SEQ ID NO 10
<211> LENGTH: 256
<212> TYPE: PRT
<213> ORGANISM: Artificial Sequence
<220> FEATURE:
<223> OTHER INFORMATION: MSP1E2

<400> SEQUENCE: 10

Met Gly His His His His His His Ile Glu Gly Arg Leu Lys Leu Leu
1               5                   10                  15
```

```
Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Tyr Leu Asp Asp Phe Gln Lys Lys Trp Gln Glu Glu Met Glu Leu Tyr
        115                 120                 125

Arg Gln Lys Val Glu Pro Leu Arg Ala Glu Leu Gln Glu Gly Ala Arg
    130                 135                 140

Gln Lys Leu His Glu Leu Gln Glu Lys Leu Ser Pro Leu Gly Glu Glu
145                 150                 155                 160

Met Arg Asp Arg Ala Arg Ala His Val Asp Ala Leu Arg Thr His Leu
                165                 170                 175

Ala Pro Tyr Ser Asp Glu Leu Arg Gln Arg Leu Ala Ala Arg Leu Glu
            180                 185                 190

Ala Leu Lys Glu Asn Gly Gly Ala Arg Leu Ala Glu Tyr His Ala Lys
        195                 200                 205

Ala Thr Glu His Leu Ser Thr Leu Ser Glu Lys Ala Lys Pro Ala Leu
    210                 215                 220

Glu Asp Leu Arg Gln Gly Leu Leu Pro Val Leu Glu Ser Phe Lys Val
225                 230                 235                 240

Ser Phe Leu Ser Ala Leu Glu Glu Tyr Thr Lys Lys Leu Asn Thr Gln
                245                 250                 255


<210> SEQ ID NO 11
<211> LENGTH: 278
<212> TYPE: PRT
<213> ORGANISM: Artificial Sequence
<220> FEATURE:
<223> OTHER INFORMATION: MSP1E3

<400> SEQUENCE: 11

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125
```

```
Arg Thr His Leu Ala Pro Tyr Leu Asp Asp Phe Gln Lys Lys Trp Gln
    130                 135                 140

Glu Glu Met Glu Leu Tyr Arg Gln Lys Val Glu Pro Leu Arg Ala Glu
145                 150                 155                 160

Leu Gln Glu Gly Ala Arg Gln Lys Leu His Glu Leu Gln Glu Lys Leu
                165                 170                 175

Ser Pro Leu Gly Glu Glu Met Arg Asp Arg Ala Arg Ala His Val Asp
            180                 185                 190

Ala Leu Arg Thr His Leu Ala Pro Tyr Ser Asp Glu Leu Arg Gln Arg
        195                 200                 205

Leu Ala Ala Arg Leu Glu Ala Leu Lys Glu Asn Gly Gly Ala Arg Leu
    210                 215                 220

Ala Glu Tyr His Ala Lys Ala Thr Glu His Leu Ser Thr Leu Ser Glu
225                 230                 235                 240

Lys Ala Lys Pro Ala Leu Glu Asp Leu Arg Gln Gly Leu Leu Pro Val
                245                 250                 255

Leu Glu Ser Phe Lys Val Ser Phe Leu Ser Ala Leu Glu Glu Tyr Thr
            260                 265                 270

Lys Lys Leu Asn Thr Gln
        275


<210> SEQ ID NO 12
<211> LENGTH: 278
<212> TYPE: PRT
<213> ORGANISM: Artificial Sequence
<220> FEATURE:
<223> OTHER INFORMATION: MSP1E3D1

<400> SEQUENCE: 12

Met Gly His His His His His His His Asp Tyr Asp Ile Pro Thr Thr
1               5                   10                  15

Glu Asn Leu Tyr Phe Gln Gly Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Leu Asp Asp Phe Gln Lys Lys Trp Gln
    130                 135                 140

Glu Glu Met Glu Leu Tyr Arg Gln Lys Val Glu Pro Leu Arg Ala Glu
145                 150                 155                 160

Leu Gln Glu Gly Ala Arg Gln Lys Leu His Glu Leu Gln Glu Lys Leu
                165                 170                 175

Ser Pro Leu Gly Glu Glu Met Arg Asp Arg Ala Arg Ala His Val Asp
            180                 185                 190

Ala Leu Arg Thr His Leu Ala Pro Tyr Ser Asp Glu Leu Arg Gln Arg
        195                 200                 205
```

```
Leu Ala Ala Arg Leu Glu Ala Leu Lys Glu Asn Gly Gly Ala Arg Leu
    210                 215                 220

Ala Glu Tyr His Ala Lys Ala Thr Glu His Leu Ser Thr Leu Ser Glu
225                 230                 235                 240

Lys Ala Lys Pro Ala Leu Glu Asp Leu Arg Gln Gly Leu Leu Pro Val
                245                 250                 255

Leu Glu Ser Phe Lys Val Ser Phe Leu Ser Ala Leu Glu Glu Tyr Thr
            260                 265                 270

Lys Lys Leu Asn Thr Gln
        275


<210> SEQ ID NO 13
<211> LENGTH: 414
<212> TYPE: PRT
<213> ORGANISM: Artificial Sequence
<220> FEATURE:
<223> OTHER INFORMATION: MSP2

<400> SEQUENCE: 13

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln Gly Thr Leu Lys Leu Leu Asp Asn Trp Asp Ser Val
    210                 215                 220

Thr Ser Thr Phe Ser Lys Leu Arg Glu Gln Leu Gly Pro Val Thr Gln
225                 230                 235                 240

Glu Phe Trp Asp Asn Leu Glu Lys Glu Thr Glu Gly Leu Arg Gln Glu
                245                 250                 255

Met Ser Lys Asp Leu Glu Glu Val Lys Ala Lys Val Gln Pro Tyr Leu
            260                 265                 270

Asp Asp Phe Gln Lys Lys Trp Gln Glu Glu Met Glu Leu Tyr Arg Gln
        275                 280                 285
```

```
Lys Val Glu Pro Leu Arg Ala Glu Leu Gln Glu Gly Ala Arg Gln Lys
    290                 295                 300

Leu His Glu Leu Gln Glu Lys Leu Ser Pro Leu Gly Glu Glu Met Arg
305                 310                 315                 320

Asp Arg Ala Arg Ala His Val Asp Ala Leu Arg Thr His Leu Ala Pro
                325                 330                 335

Tyr Ser Asp Glu Leu Arg Gln Arg Leu Ala Ala Arg Leu Glu Ala Leu
            340                 345                 350

Lys Glu Asn Gly Gly Ala Arg Leu Ala Glu Tyr His Ala Lys Ala Thr
        355                 360                 365

Glu His Leu Ser Thr Leu Ser Glu Lys Ala Lys Pro Ala Leu Glu Asp
    370                 375                 380

Leu Arg Gln Gly Leu Leu Pro Val Leu Glu Ser Phe Lys Val Ser Phe
385                 390                 395                 400

Leu Ser Ala Leu Glu Glu Tyr Thr Lys Lys Leu Asn Thr Gln
                405                 410


<210> SEQ ID NO 14
<211> LENGTH: 403
<212> TYPE: PRT
<213> ORGANISM: Artificial Sequence
<220> FEATURE:
<223> OTHER INFORMATION: MSP2N1

<400> SEQUENCE: 14

Met Gly His His His His His His His Asp Tyr Asp Ile Pro Thr Thr
1               5                   10                  15

Glu Asn Leu Tyr Phe Gln Gly Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln Gly Thr Ser Thr Phe Ser Lys Leu Arg Glu Gln Leu
    210                 215                 220

Gly Pro Val Thr Gln Glu Phe Trp Asp Asn Leu Glu Lys Glu Thr Glu
225                 230                 235                 240
```

Gly Leu Arg Gln Glu Met Ser Lys Asp Leu Glu Glu Val Lys Ala Lys
245 250 255

Val Gln Pro Tyr Leu Asp Asp Phe Gln Lys Lys Trp Gln Glu Glu Met
260 265 270

Glu Leu Tyr Arg Gln Lys Val Glu Pro Leu Arg Ala Glu Leu Gln Glu
275 280 285

Gly Ala Arg Gln Lys Leu His Glu Leu Gln Glu Lys Leu Ser Pro Leu
290 295 300

Gly Glu Glu Met Arg Asp Arg Ala Arg Ala His Val Asp Ala Leu Arg
305 310 315 320

Thr His Leu Ala Pro Tyr Ser Asp Glu Leu Arg Gln Arg Leu Ala Ala
325 330 335

Arg Leu Glu Ala Leu Lys Glu Asn Gly Gly Ala Arg Leu Ala Glu Tyr
340 345 350

His Ala Lys Ala Thr Glu His Leu Ser Thr Leu Ser Glu Lys Ala Lys
355 360 365

Pro Ala Leu Glu Asp Leu Arg Gln Gly Leu Leu Pro Val Leu Glu Ser
370 375 380

Phe Lys Val Ser Phe Leu Ser Ala Leu Glu Glu Tyr Thr Lys Lys Leu
385 390 395 400

Asn Thr Gln

<210> SEQ ID NO 15
<211> LENGTH: 392
<212> TYPE: PRT
<213> ORGANISM: Artificial Sequence
<220> FEATURE:
<223> OTHER INFORMATION: MSP2N2

<400> SEQUENCE: 15

Met Gly His His His His His His His Asp Tyr Asp Ile Pro Thr Thr
1 5 10 15

Glu Asn Leu Tyr Phe Gln Gly Ser Thr Phe Ser Lys Leu Arg Glu Gln
20 25 30

Leu Gly Pro Val Thr Gln Glu Phe Trp Asp Asn Leu Glu Lys Glu Thr
35 40 45

Glu Gly Leu Arg Gln Glu Met Ser Lys Asp Leu Glu Glu Val Lys Ala
50 55 60

Lys Val Gln Pro Tyr Leu Asp Asp Phe Gln Lys Lys Trp Gln Glu Glu
65 70 75 80

Met Glu Leu Tyr Arg Gln Lys Val Glu Pro Leu Arg Ala Glu Leu Gln
85 90 95

Glu Gly Ala Arg Gln Lys Leu His Glu Leu Gln Glu Lys Leu Ser Pro
100 105 110

Leu Gly Glu Glu Met Arg Asp Arg Ala Arg Ala His Val Asp Ala Leu
115 120 125

Arg Thr His Leu Ala Pro Tyr Ser Asp Glu Leu Arg Gln Arg Leu Ala
130 135 140

Ala Arg Leu Glu Ala Leu Lys Glu Asn Gly Gly Ala Arg Leu Ala Glu
145 150 155 160

Tyr His Ala Lys Ala Thr Glu His Leu Ser Thr Leu Ser Glu Lys Ala
165 170 175

Lys Pro Ala Leu Glu Asp Leu Arg Gln Gly Leu Leu Pro Val Leu Glu
180 185 190

```
Ser Phe Lys Val Ser Phe Leu Ser Ala Leu Glu Glu Tyr Thr Lys Lys
        195                 200                 205

Leu Asn Thr Gln Gly Thr Pro Val Thr Gln Glu Phe Trp Asp Asn Leu
    210                 215                 220

Glu Lys Glu Thr Glu Gly Leu Arg Gln Glu Met Ser Lys Asp Leu Glu
225                 230                 235                 240

Glu Val Lys Ala Lys Val Gln Pro Tyr Leu Asp Asp Phe Gln Lys Lys
                245                 250                 255

Trp Gln Glu Glu Met Glu Leu Tyr Arg Gln Lys Val Glu Pro Leu Arg
            260                 265                 270

Ala Glu Leu Gln Glu Gly Ala Arg Gln Lys Leu His Glu Leu Gln Glu
        275                 280                 285

Lys Leu Ser Pro Leu Gly Glu Glu Met Arg Asp Arg Ala Arg Ala His
    290                 295                 300

Val Asp Ala Leu Arg Thr His Leu Ala Pro Tyr Ser Asp Glu Leu Arg
305                 310                 315                 320

Gln Arg Leu Ala Ala Arg Leu Glu Ala Leu Lys Glu Asn Gly Gly Ala
                325                 330                 335

Arg Leu Ala Glu Tyr His Ala Lys Ala Thr Glu His Leu Ser Thr Leu
            340                 345                 350

Ser Glu Lys Ala Lys Pro Ala Leu Glu Asp Leu Arg Gln Gly Leu Leu
        355                 360                 365

Pro Val Leu Glu Ser Phe Lys Val Ser Phe Leu Ser Ala Leu Glu Glu
    370                 375                 380

Tyr Thr Lys Lys Leu Asn Thr Gln
385                 390


<210> SEQ ID NO 16
<211> LENGTH: 397
<212> TYPE: PRT
<213> ORGANISM: Artificial Sequence
<220> FEATURE:
<223> OTHER INFORMATION: MSP2N3

<400> SEQUENCE: 16

Met Gly His His His His His His His Asp Tyr Asp Ile Pro Thr Thr
1               5                   10                  15

Glu Asn Leu Tyr Phe Gln Gly Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160
```

```
Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln Gly Thr Arg Glu Gln Leu Gly Pro Val Thr Gln Glu
    210                 215                 220

Phe Trp Asp Asn Leu Glu Lys Glu Thr Glu Gly Leu Arg Gln Glu Met
225                 230                 235                 240

Ser Lys Asp Leu Glu Glu Val Lys Ala Lys Val Gln Pro Tyr Leu Asp
                245                 250                 255

Asp Phe Gln Lys Lys Trp Gln Glu Glu Met Glu Leu Tyr Arg Gln Lys
            260                 265                 270

Val Glu Pro Leu Arg Ala Glu Leu Gln Glu Gly Ala Arg Gln Lys Leu
        275                 280                 285

His Glu Leu Gln Glu Lys Leu Ser Pro Leu Gly Glu Glu Met Arg Asp
    290                 295                 300

Arg Ala Arg Ala His Val Asp Ala Leu Arg Thr His Leu Ala Pro Tyr
305                 310                 315                 320

Ser Asp Glu Leu Arg Gln Arg Leu Ala Ala Arg Leu Glu Ala Leu Lys
                325                 330                 335

Glu Asn Gly Gly Ala Arg Leu Ala Glu Tyr His Ala Lys Ala Thr Glu
            340                 345                 350

His Leu Ser Thr Leu Ser Glu Lys Ala Lys Pro Ala Leu Glu Asp Leu
        355                 360                 365

Arg Gln Gly Leu Leu Pro Val Leu Glu Ser Phe Lys Val Ser Phe Leu
    370                 375                 380

Ser Ala Leu Glu Glu Tyr Thr Lys Lys Leu Asn Thr Gln
385                 390                 395


<210> SEQ ID NO 17
<211> LENGTH: 258
<212> TYPE: PRT
<213> ORGANISM: Artificial Sequence
<220> FEATURE:
<223> OTHER INFORMATION: engineered ApoA1

<400> SEQUENCE: 17

Met His His His His His His Gly Leu Val Pro Arg Gly Ser Ile Asp
1               5                   10                  15

Asp Pro Pro Gln Ser Pro Trp Asp Arg Val Lys Asp Leu Ala Thr Val
            20                  25                  30

Tyr Val Asp Val Leu Lys Asp Ser Gly Arg Asp Tyr Val Ser Gln Phe
        35                  40                  45

Glu Gly Ser Ala Leu Gly Lys Gln Leu Asn Leu Lys Leu Leu Asp Asn
    50                  55                  60

Trp Asp Ser Val Thr Ser Thr Phe Ser Lys Leu Arg Glu Gln Leu Gly
65                  70                  75                  80

Pro Val Thr Gln Glu Phe Trp Asp Asn Leu Glu Lys Glu Thr Glu Gly
                85                  90                  95

Leu Arg Gln Glu Met Ser Lys Asp Leu Glu Glu Val Lys Ala Lys Val
            100                 105                 110

Gln Pro Tyr Leu Asp Asp Phe Gln Lys Lys Trp Gln Glu Glu Met Glu
        115                 120                 125
```

-continued

```
Leu Tyr Arg Gln Lys Val Glu Pro Leu Arg Ala Glu Leu Gln Glu Gly
    130                 135                 140

Ala Arg Gln Lys Leu His Glu Leu Gln Glu Lys Leu Ser Pro Leu Gly
145                 150                 155                 160

Glu Glu Met Arg Asp Arg Ala Arg Ala His Val Asp Ala Leu Arg Thr
                165                 170                 175

His Leu Ala Pro Tyr Ser Asp Glu Leu Arg Gln Arg Leu Ala Ala Arg
            180                 185                 190

Leu Glu Ala Leu Lys Glu Asn Gly Gly Ala Arg Leu Ala Glu Tyr His
        195                 200                 205

Ala Lys Ala Thr Glu His Leu Ser Thr Leu Ser Glu Lys Ala Lys Pro
    210                 215                 220

Ala Leu Glu Asp Leu Arg Gln Gly Leu Leu Pro Val Leu Glu Ser Phe
225                 230                 235                 240

Lys Val Ser Phe Leu Ser Ala Leu Glu Glu Tyr Thr Lys Lys Leu Asn
                245                 250                 255

Thr Gln
```

PHARMACEUTICAL COMPOSITION COMPRISING NANOPERFORATOR FOR PREVENTING OR TREATING VIRAL INFECTIOUS DISEASES

CROSS-REFERENCE TO RELATED APPLICATIONS

This application is a 371 of PCT/KR2017/007602, filed Jul. 14, 2017, which claims the benefit of priority from Korean Patent Application No. 10-2016-0090012, filed Jul. 15, 2016 and Korean Patent Application No. 10-2017-0089655, filed Jul. 14, 2017, the contents of each of which are incorporated herein by reference.

TECHNICAL FIELD

The present invention relates to a nano-perforator including a lipid bilayer nanodisc and a membrane scaffold protein, and a composition for preventing or treating viral infections, which includes the nano-perforator, and more particularly, to a pharmaceutical composition for preventing or treating viral infections, which includes a nano-perforator in which a lipid bilayer is surrounded by a membrane scaffold protein, a method of preventing or treating viral infections, which includes administering the pharmaceutical composition, and a method of screening for a receptor for a virus surface antigen by using the nano-perforator.

BACKGROUND ART

An influenza virus is an RNA virus belonging to the family Orthomyxoviridae, which is divided into three types: A, B, and C. Among these types, while the influenza B and C viruses infect only humans, the influenza A virus infects humans, horses, pigs, other mammals, and various types of poultry and wild birds. The serotype of the influenza A virus is divided according to the type of two viral surface proteins, i.e., hemagglutinin (HA) and neuraminidase (NA), and to date, 144 types of viral surface proteins (16 types of the HA protein and 9 types of the NA protein) are known. HA plays a role in attaching a virus to somatic cells, and NA allows a virus to penetrate into cells.

The swine influenza A (H1N1) virus, which has recently drawn attention, is also referred to as "swine flu" or "swine flu virus," and is a new type of virus in which genetic materials of human, pig, and avian influenza viruses are mixed.

As viral infectious therapeutic agents developed so far, an amantadine- or rimantadine-based M2 ion channel inhibitor and an oseltamivir (Tamiflu®)- or zanamivir (Relenza®)-based neuraminidase inhibitor are known, but these therapeutic agents have limited effects. That is, it is known that variant viruses having resistance to amantadine- or rimantadine-based derivative compounds are rapidly produced, H5N1-type influenza viruses, which are detected in some areas, have resistance to amantadine- or rimantadine-based compounds, and the influenza B virus is not sensitive to amantadine derivatives. It is also known that the number of viruses having resistance to oseltamivir- or zanamivir-based derivative compounds has increased, and these resistant viruses occur frequently in children.

Studies have been actively conducted to develop a novel therapeutic agent that does not have the above-described problems in existing treatments of viral infections. For example, Korean Patent Registration No. 1334143 discloses a composition for preventing or treating a cold, avian influenza, swine influenza, or swine flu, which includes a Polygala karensium extract and a xanthone-based compound isolated therefrom. However, these agents have low anti-viral activity, and thus are unable to exhibit an effective effect of preventing or treating swine flu.

Therefore, there is an urgent need to develop a new anti-influenza agent that can be generally applied to all variant viruses and replace existing viral inhibitors.

DESCRIPTION OF EMBODIMENTS

Technical Problem

An object of the present invention is to provide a nano-perforator including a lipid bilayer nanodisc and a membrane scaffold protein.

Another object of the present invention is to provide a pharmaceutical composition for preventing or treating viral infection, which includes the above-described nano-perforator, or an anti-viral use of the nano-perforator.

Still another object of the present invention is to provide a method of preventing or treating viral infection, which includes administering the above-described pharmaceutical composition.

Yet another object of the present invention is to provide a method of screening for a virus surface antigen receptor by using the above-described nano-perforator.

Technical Solution

According to the present invention, it can be confirmed that when a lipid bilayer nano-perforator having a structure in which a lipid bilayer is surrounded by a membrane scaffold protein is used, a novel effect of preventing or treating influenza virus infection is exhibited by preventing the infection of the influenza viruses or inhibiting the proliferation of infected influenza viruses, and such an effect is further enhanced when a receptor capable of binding to a virus surface antigen is inserted into the lipid bilayer. In addition, the inventors of the present invention confirmed that the nano-perforator damaged the structural stability of a virus having a lipid bilayer envelope, and thus could exhibit anti-viral activity.

In addition, the inventors of the present invention have focused on the infection mechanisms of viruses having lipid bilayer envelopes. The viruses generally include membrane-binding proteins used as a surface antigen on lipid bilayer envelopes, and it is known that host cells are infected with the viruses through the membrane-binding proteins. When a nano-perforator, in which a receptor for a membrane protein of such a virus is inserted into a lipid bilayer region, is used, the nano-perforator may disturb the infection pathways of these viruses. To confirm this, by using an influenza virus as an example of the viruses having lipid bilayer envelopes, and using a nano-perforator including or not including, as a receptor for membrane proteins of viruses, a ganglioside including sialic acid of a membrane receptor of epithelial cells of the respiratory system (lungs and bronchial tubes), which is capable of binding to hemagglutinin (HA) known as a major surface antigen of an influenza virus, an effect of the nano-perforator on infection processes of the influenza virus was examined. As a result, it was confirmed that the nano-perforator not including a ganglioside exhibited anti-viral activity against an influenza virus, and the nano-perforator including a ganglioside exhibited further enhanced anti-viral activity.

Since the lipid bilayer nano-perforator according to the present invention may exhibit anti-viral activity against viruses having lipid bilayer envelopes, the nano-perforator may exhibit an effect of preventing or treating infections caused by the viruses having lipid bilayer envelopes, and such anti-viral activity of the nano-perforator, for example, viral envelope perforation activity, has never been known so far.

To achieve the above-described objects, according to an embodiment of the present invention, there is provided a nano-perforator including a lipid bilayer nanodisc and a membrane scaffold protein surrounding an outer circumferential surface of a lipid bilayer of the nanodisc.

In one embodiment of the present invention, the nano-perforator may have a diameter of 1 nm to 50 nm, more preferably 10 nm to 20 nm, but the diameter of the nano-perforator is not particularly limited as long as it enables the nano-perforator to function properly.

The nano-perforator according to the present invention may inhibit the formation of an endosome by endocytosis of a virus by binding to a virus envelope (primary inhibition), and although a virus is endocytosed into a cell, the nano-perforator may act as a perforator that forms a hole in an envelope of the endocytosed virus (secondary inhibition), and thus may inhibit the proliferation of the virus such that RNA in the virus is released into an endosome via the hole and inactivated by the pH inside the endosome, thus exhibiting an effect of secondarily inhibiting viral infection.

The nano-perforator of the present invention may inhibit viral proliferation independently of virus mutation, and in particular, does not include a substance inducing a specific response in vivo, and thus may secure safety.

The term "nano-perforator" as used herein refers to a nano-scale material that includes a lipid bilayer nanodisc and a membrane scaffold protein surrounding an outer circumferential surface of a lipid bilayer of the lipid bilayer nanodisc, and is able to perforate a virus envelope. The nano-perforator may include a disc-type unilamellar lipid bilayer, i.e., a lipid bilayer nanodisc, and may be a complex having a structure in which the outer circumferential surface of the lipid bilayer is surrounded by one or more membrane scaffold proteins, e.g., two membrane scaffold proteins.

The term "lipid bilayer nanodisc" as used herein refers to a material including a lipid bilayer and having a unilamellar disc shape, and the nanodisc has an open system in which both opposite surfaces of the lipid bilayer are open to the outside. That is, this may mean that the nanodisc itself according to the present does not form a closed space having the lipid bilayer as an inner core.

Lipids constituting the lipid bilayer nanodisc may be phospholipids including, for example, $C_1$-$C_{50}$, preferably $C_5$-$C_{30}$ lipid tails.

The lipid may be, for example, one or more selected from the group consisting of phosphatidylcholines, phosphatidylglycerols, phosphatidylethanolamines, phosphatidylserines, and cholesterol, but is not particularly limited as long as it is a lipid capable of constituting the bilayer.

The phosphatidylcholine may be 1,2-dioleoyl-sn-glycero-3-phosphocholine (DOPC), 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1-palmitoyl-2-oleoyl-sn-glycero-3-phosphocholine (POPC), C13PC, 1,2-didecanoyl-sn-glycero-3-phosphocholine (DDPC), 1,2-distearoyl-sn-glycero-3-phosphocholine (DSPC), 1,2-dierucoyl-sn-glycero-3-phosphocholine (DEPC), 1,2-dilinoleoyl-sn-glycero-3-phosphocholine (DLOPC), egg phosphatidylcholine (EPC), 1-myristoyl-2-stearoyl-sn-glycero-3-phosphocholine (MSPC), 1-palmitoyl-2-myristoyl-sn-glycero-3-phosphocholine (PMPC), 1-palmitoyl-2-stearoyl-sn-glycero-3-phosphocholine (PSPC), 1-stearoyl-2-myristoyl-sn-glycero-3-phosphocholine (SMPC), or 1-stearoyl-2-palmitoyl-sn-glycero-3-phosphocholine (SPPC). The phosphatidylglycerol may be 1,2-dimyristoyl-sn-glycero-3 [phospho-rac-(1-glycerol)] (DMPG), 1,2-dipalmitoyl-sn-glycero-3 [phospho-rac-(1-glycerol)] (DPPG), 1,2-di stearoyl-sn-glycero-3 [phospho-rac-(1-gycerol)] (DSPG), 1-palmitoyl-2-oleoyl-sn-glycero-3 [phospho-rac-(1-glycerol)] (POPG), 1,2-dierucoyl-sn-glycero-3 [phospho-rac-(1-glycerol)] (DEPG), 1,2-dilauroyl-sn-glycero-3 [phospho-rac-(1-glycerol)] (DLPG), 1,2-dioleoyl-sn-glycero-3 [phospho-rac-(1-glycerol)] (DOPG), or 1,2-distearoyl-sn-glycero-3 [phospho-rac-(1-glycerol)] (DSPG). The phosphatidylethanolamine may be 1,2-dimyristoyl-sn-glycero-3-phosphoethanolamine (DMPE), 1,2-dipalmitoyl-sn-glycero-3-phosphoethanolamine (DPPE), 1,2-distearoyl-sn-glycero-3-phosphoethanolamine (D SPE), 1,2-dioleoyl-sn-glycero-3-phosphoethanolamine (DOPE), 1,2-dierucoyl-sn-glycero-3-phosphoethanolamine (DEPE), 1,2-dilauroyl-sn-glycero-3-phosphoethanolamine (DLPE), or 1-palmitoyl-2-oleoyl-sn-glycero-3-phosphoethanolamine (POPE). The phosphatidylserine may be 1,2-dioleoyl-sn-glycero-3-phosphoserine (DOPS), 1,2-dilauroyl-sn-glycero-3-phosphoserine (DLPS), 1,2-dimyristoyl-sn-glycero-3-phosphoserine (DMPS), 1,2-dipalmitoyl-sn-glycero-3-phosphoserine (DPPS), 1,2-distearoyl-sn-glycero-3-phosphoserine (DSPS), or POPS.

The lipid constituting the lipid bilayer nanodisc may include, in addition to the phospholipid, one or more selected from the group consisting of a neutral fat (e.g., triglycerides), cholesterol or a derivative thereof, and a saccharolipid (e.g., gangliosides).

The lipid bilayer nanodisc has a disc shape having an open system in which both opposite surfaces of the lipid bilayer are exposed to the outside, and thus is distinguished from a sphere-type liposome including a hydrophilic core inside thereof and having a closed system in which only one of both opposite sides of a lipid bilayer is exposed to the outside. The liposome may form a closed space having the lipid bilayer as an inner core.

The nano-perforator according to the present invention includes a membrane scaffold protein surrounding the outer circumferential surface of the nanodisc. The term "membrane scaffold protein" as used herein refers to an amphipathic helical protein and means a protein capable of constituting the shape of the nano-perforator including a lipid bilayer according to the present invention by surrounding the outer circumferential surface of the lipid bilayer. In the present invention, the membrane scaffold protein surrounding the outer circumferential surface of the lipid bilayer may be an amphipathic protein including a hydrophobic region and a hydrophilic region. The nano-perforator may be formed such that the hydrophobic region (e.g., hydrophobic amino acid) of the membrane scaffold protein binds to a hydrophobic region (e.g., lipid) of the lipid bilayer nanodisc, and the hydrophilic region (e.g., hydrophilic amino acid) of the membrane scaffold protein is exposed to the outside. For example, the membrane scaffold protein may be an amphipathic protein having a helical structure.

Examples of the membrane scaffold protein may include apolipoproteins (Yelena V. Grinkova, et al., Protein Engineering, Design & Selection, 23(11): 843-848, 2010), such as apolipoprotein A1 or a mutant protein derived from an amino acid sequence of the apolipoprotein A1.

In the present invention, the membrane scaffold protein is not particularly limited as long as it is capable of constituting the nano-perforator of the present invention, but may be, for example, an apolipoprotein or a mutant thereof. The apolipoprotein (Apo) may be one or more selected from the group consisting of apolipoprotein A1 (ApoA-1), apolipoprotein A2 (ApoA-2), apolipoprotein B (ApoB), apolipoprotein C (ApoC), and apolipoprotein E (ApoE). For example, the ApoA-1 may include an amino acid sequence of SEQ ID NO: 1, the ApoA-2 may include an amino acid sequence of SEQ ID NO: 2, and the ApoB may include an amino acid sequence of SEQ ID NO: 3. The ApoC may be one or more selected from the group consisting of ApoC1 and ApoC3, and for example, the ApoC1 may include an amino acid sequence of SEQ ID NO: 4, and the ApoC3 may include an amino acid sequence of SEQ ID NO: 5.

Specific examples of the membrane scaffold protein include mutants of apolipoprotein A1, such as membrane scaffold protein 1 (MSP1) (SEQ ID NO: 6), MSP1D1 (SEQ ID NO: 7), MSP1D2 (SEQ ID NO: 8), MSP1E1 (SEQ ID NO: 9), MSP1E2 (SEQ ID NO: 10), MSP1E3 (SEQ ID NO: 11), MSP1E3D1 (SEQ ID NO: 12), MSP2 (SEQ ID NO: 13), MSP2N1 (SEQ ID NO: 14), MSP2N2 (SEQ ID NO: 15), MSP2N3 (SEQ ID NO: 16), and the like.

The ApoA-1 refers to a protein that consists of a single polypeptide having a molecular weight of 28 kDa and consisting of 243 amino acids, has 8 repeating unit domains consisting of 11 amino acids or 22 amino acids, and a proportion of alpha-helix in a secondary structure constituting a high density lipoprotein (HDL) of 60% to 75%. The ApoA-1 is known to be used as a constituent of a HDL that plays a direct role in removing cholesterol mainly from peripheral tissues and transporting the cholesterol to the liver or other lipoproteins.

ApoE is a protein consisting of a single polypeptide having a molecular weight of 33 kDa and consisting of 299 amino acids and is involved in transportation of cholesterol like ApoA-1.

The term “virus having a lipid bilayer envelope (or membrane)” as used herein refers to a virus having an envelope of a lipid bilayer among viruses, and an antigen protein involved in infection and proliferation of the virus is included in the form of a membrane-binding protein in the lipid bilayer. The virus having a lipid bilayer envelope is not particularly limited as long as the nano-perforator according to the present invention exhibits anti-viral activity, but as an example, the virus may be a virus belonging to the family Bunyaviridae, the family Coronaviridae, the family Filoviridae, the family Flaviviridae, the family Hepadnaviridae, the family Orthomyxoviridae, the family Poxviridae, the family Rhabdoviridae, the family Retroviridae, the family Togaviridae, the family Herpesviridae, or the like. As another example, the virus may be Sin Nombre Hantavirus belonging to the family Bunyaviridae, or the like; a coronavirus belonging to the family Coronaviridae and involved in various acute respiratory syndromes, or the like; Ebola virus, Marburg virus, belonging to the family Filoviridae, or the like; West Nile virus, Yellow Fever virus, Dengue Fever virus, Hepatitis C virus, belonging to the family Flaviviridae, or the like; Hepatitis B virus belonging to the family Hepadnaviridae, or the like; Herpes Simplex 1 virus, Herpes Simplex 2 virus, belonging to the family Herpesviridae, or the like; an influenza virus belonging to the family Orthomyxoviridae, or the like; Smallpox virus, Vaccinia virus, Molluscum contagiosum virus, Monkeypox virus, belonging to the family Poxviridae, or the like; Rabies virus belonging to the family Rhabdoviridae, or the like; Human Immunodeficiency virus (HIV) belonging to the family Retroviridae, or the like; Chikungunya virus belonging to the family Togaviridae, or the like; or Pseudorabies virus, HHV virus, belonging to the family Herpesviriae, or the like, and as another example, the virus may be an influenza virus belonging to the family Orthomyxoviridae. For example, the virus may be a virus having affinity with a receptor (e.g., a ganglioside) included in the nano-perforator.

The term “influenza virus” as used herein refers to an RNA virus belonging to the family Orthomyxoviridae, which is divided into three types: A, B, and C. The serotypes of the influenza A virus are classified according to the types of hemagglutinin (HA) and neuraminidase (NA), which are two virus surface proteins, and to date, 144 types (16 types of HA protein and 9 types of NA protein) are known.

The nano-perforator according to the present invention may further include, in addition to the nanodisc, a receptor for a surface antigen of the virus having a lipid bilayer envelope. The nano-perforator of the present invention may include one or more receptors.

The term “surface antigen” as used herein, which is also referred to as a cell membrane antigen, refers to a membrane binding protein present in cell membranes and exhibiting antigenicity.

In the present invention, the surface antigen may be construed as meaning a membrane binding protein bound to a lipid bilayer of a virus having a lipid bilayer envelope, and for example, may be, but is not particularly limited to, hemagglutinin (HA) or neuraminidase (NA), which is a surface antigen of an influenza virus, or the like. The term “hemagglutinin (HA)” as used herein refers to a transmembrane protein, which is a surface antigen of an influenza virus and consists of a HA1 subunit and a HA2 subunit that can be cleaved by trypsin. It is known that the HA1 subunit binds to sialic acid, and the HA2 subunit induces cell membrane fusion under low pH conditions.

The term “receptor for a surface antigen” as used herein refers to a receptor capable of binding to the surface antigen, and the receptor may be an antibody against the surface antigen, or another cell membrane binding protein to which the surface antigen can bind.

In the present invention, the receptor for a surface antigen may be construed as meaning a receptor that is present on a surface of a host cell that can be infected with a virus having a lipid bilayer envelope and is capable of binding to a surface antigen of the virus. The receptor and the surface antigen of the virus may be bound to each other by various interactions such as hydrogen bonding, ionic bonding, and the like, and for example, a receptor binding site of the outermost surface of a HA1 subunit of hemagglutinin of the virus may bind to sialic acid. Thus, the receptor of the present invention may be a receptor that allows specific or affinity binding to a target virus, e.g., a virus including hemagglutinin and/or neuraminidase.

The type of the receptor for a surface antigen is not particularly limited, but may include sialic acid and/or a functional group having a sialic acid-like function (e.g., a sialic acid-mimic peptide). The receptor may be one or more selected from the group consisting of sialyloligosaccharides, e.g., gangliosides, glycoproteins, and polysialic acid, but is not particularly limited as long as it is a receptor including sialic acid.

The receptor itself may be inserted into or bind to the lipid bilayer, or the receptor may be inserted into or bind to the lipid bilayer via a linker.

The receptor itself or a linker to which the receptor is bound may bind to lipids of the lipid bilayer of the nanodisc by various interactions such as hydrogen bonding, ionic bonding, covalent bonding, disulfide bonding, and the like.

An example of the receptor may be sialic acid present in the cell membrane of a respiratory cell and capable of binding to hemagglutinin, which is a surface antigen of an influenza virus, and may include a ganglioside including the sialic acid and bound to a cell membrane.

The term "ganglioside" as used herein refers to a compound having a structure in which one or more sialic acids are linked to a sugar chain of a glycosphingolipid via a specific bond (α-2,3 bond or α-2,6 bond), and the ganglioside may include both a form including α-2,3-linked sialic acid and a form including α-2,6-linked sialic acid. For example, the ganglioside of the present invention may be GM1, GM2, and/or GM3 that include(s) one N-acetylneuraminic acid or sialic acid residue, GD1a, GD1b, GD2, and/or GD3 that include(s) two N-acetylneuraminic acids, GT1b and/or GT3 that include(s) three N-acetylneuraminic acids, and GQ1 including four N-acetylneuraminic acids.

In the present invention, the receptor, for example, a ganglioside may be inserted into a lipid bilayer nanodisc region of the lipid bilayer nano-perforator and serve to bind to the HA of the virus having a lipid bilayer envelope.

In one embodiment of the present invention, a molar ratio of one or more selected from the group consisting of a lipid and a surface antigen receptor, which constitute a lipid bilayer included in the nano-perforator, to the membrane scaffold protein ([(the number of moles of the lipid of the lipid bilayer nanodisc)+(the number of moles of the receptor for the surface antigen)]: the number of moles of the membrane scaffold protein) may range from 10:1 to 800:1, preferably 50:1 to 500:1, and more preferably 50:1 to 150:1, and may be, for example, 65:1 or 125:1. For example, the molar ratio may be a molar ratio of the lipid of the nanodisc to the membrane scaffold protein, or a ratio of the sum of the number of moles of the lipid of the nanodisc and the number of moles of the surface antigen receptor to the number of moles of the membrane scaffold protein.

The surface antigen receptor, for example, a ganglioside included in the nano-perforator of the present invention may be included in an amount of 0.01 mol % to 99 mol %, preferably 1 mol % to 90 mol %, and more preferably 15 mol % or more or 10 mol % to 50 mol %, with respect to 100% of a total number of moles of the nanodisc (the sum of the number of moles of the lipid and the number of moles of the receptor).

A structure of a nano-perforator according to the present invention in which a ganglioside as a receptor is inserted into a lipid bilayer is exemplarily illustrated in FIG. 1. In addition, an action mechanism of the nano-perforator including a ganglioside for exhibiting an effect of preventing or treating infections by a virus having a lipid bilayer envelope will be described in detail with reference to FIG. 3 as follows.

As described above, generally, a HA1 subunit constituting HA of the virus binds to sialic acid of a host cell membrane and infiltrates into a host cell through intracellular insertion. Meanwhile, when a cell infected with a virus is treated with the nano-perforator of the present invention, for example, the nano-perforator including a ganglioside as a receptor, HA of the virus may bind to not only a host cell membrane, but also the lipid bilayer nanodisc and/or the receptor of the nano-perforator, and when the treatment amount of the nano-perforator is increased, the proportion of the virus bound to the nano-perforator increases, and thus the infection of a host cell with the virus may be prevented. Thus, the nano-perforator may be an entry inhibitor that inhibits intracellular infiltration of the virus by acting as a decoy that mimics a receptor of the host cell (primary inhibition).

The intracellular infection pathway of a virus with which a host cell is infected, for example, an influenza virus, may be disturbed using the nano-perforator of the present invention, e.g., the nano-perforator including a ganglioside as a surface antigen receptor, thereby inhibiting the proliferation of the virus.

In membrane fusion induced in the late endosome phase during endocytosis of the virus, membrane fusion may not occur between an envelope of a virus bound to the nano-perforator of the present invention and a cell membrane of a host cell, but may occur between the envelope of the virus and the lipid bilayer of the nano-perforator. Such cell membrane fusion occurs stochastically, and in a case in which a virus is bound to a host cell membrane and a plurality of nano-perforators, membrane fusion may occur between an envelope of the virus and lipid bilayers of the nano-perforators, rather than between the envelope of the virus and the host cell membrane. As such, when membrane fusion is induced, in an endosome, between the envelope of the virus and a lipid bilayer of a nano-perforator, RNA present inside the virus is released into the endosome through the membrane fusion region, and the released RNA is inactivated by the low pH inside the endosome, resulting in degradation of the virus. Thus, the nano-perforator of the present invention may be a perforator for perforating the envelope of a virus in virus-endosome membrane fusion (secondary inhibition).

That is, the nano-perforator may inhibit the formation of an endosome, which is caused by endocytosis of a virus, by binding to an envelope of the virus (primary inhibition), and although the virus is endocytosed into a cell, may exhibit an effect of secondarily inhibiting viral infection by acting as a perforator that perforates the envelope of the endocytosed virus (secondary inhibition).

Thus, when a cell infected with the virus having a lipid bilayer envelope is treated with the nano-perforator including a surface antigen receptor, e.g., a ganglioside, the nano-perforator disturbs the infection pathway of the virus, thereby inhibiting the infection of the virus, resulting in inhibition of the proliferation of the virus, and accordingly, the nano-perforator exhibits an effect of treating a disease induced by viral infection.

In summary, the nano-perforator of the present invention may inhibit the infection of a host cell with the virus having a lipid bilayer envelope or fundamentally inhibit the proliferation of the virus after infection, thus exhibiting an effect of preventing or treating a disease induced by viral infection. Accordingly, the lipid bilayer nano-perforator including a ganglioside according to the present invention may exhibit the same effect on any virus capable of binding to a host cell via sialic acid of the host cell regardless of mutation, may inhibit initial infection of the virus, and even after a host is infected with a virus, may fundamentally inhibit the proliferation of the virus. Thus, the nano-perforator of the present invention may be characterized as being independent of virus mutation. In particular, the nano-perforator does not include a substance that causes a specific response in vivo, and thus may secure safety.

According to one embodiment of the present invention, nano-perforators with or without a ganglioside on a lipid bilayer were produced, and the anti-viral activity of each nano-perforator was analyzed. As a result, it was confirmed that both the nano-perforators with or without a ganglioside on a lipid bilayer fused with an envelope of an influenza virus, releasing RNA of the influenza virus to the outside (see FIG. 9A), and both the nano-perforators with or without a ganglioside on a lipid bilayer exhibited anti-viral activity against the influenza virus, thus reducing the level of a plaque formed by the influenza virus (see FIGS. 5A, 5B, 5C, and 5D). In particular, as illustrated in FIGS. 4 and 5A, it was confirmed that although both the nano-perforators with or without a ganglioside on a lipid bilayer exhibited anti-viral activity against an influenza virus, the nano-perforator including a ganglioside on a lipid bilayer exhibited much higher anti-viral activity than that of the nano-perforator not including a ganglioside on a lipid bilayer.

Thus, it can be seen that the nano-perforator according to the present invention exhibits anti-viral activity, and a nano-perforator including a receptor for a virus surface antigen, such as a ganglioside, on a lipid bilayer exhibits further enhanced anti-viral activity.

In the present invention, according to the purpose of use, one or more markers selected from the group consisting of histidine (His), gold (Au), a fluorescent lipid, and biotin/avidin may be used in combination.

According to another embodiment of the present invention, there is provided a viral activity inhibitor or viral replication inhibitor including a lipid bilayer nanodisc and a membrane scaffold protein surrounding an outer circumferential surface of the nanodisc.

The foregoing description of the nano-perforator may be equally applied to the viral activity inhibitor or the viral replication inhibitor.

According to another embodiment of the present invention, there is provided a pharmaceutical composition for preventing or treating a viral infection caused by infection of a virus having a lipid bilayer envelope, the pharmaceutical composition including a nano-perforator including a lipid bilayer nanodisc and a membrane scaffold protein surrounding an outer circumferential surface of a lipid bilayer of the nanodisc, or a use of the nano-perforator for preventing or treating a viral infection.

The foregoing description of the nano-perforator may be equally applied to a pharmaceutical composition for treating, preventing, or alleviating one or more symptoms associated with viral infection or derived from viral infection, or for delaying the onset thereof, or a use thereof for the treatment, prevention, or alleviation of one or more symptoms associated with viral infection or derived from viral infection, or delay of the onset thereof.

As described above, since the nano-perforator according to the present invention may disturb the infection pathway of the virus having a lipid bilayer envelope or inhibit the proliferation of an infected virus, the nano-perforator may be used in preventing or treating various infections caused by infection of the virus having a lipid bilayer envelope. A composition for preventing or treating a viral infection, according to the present invention may be applied independently of virus mutation, and the nano-perforator may secure safety since it does not include a substance that induces a specific response in vivo.

The term “viral infection” as used herein refers to a disease occurring due to infection of the virus having a lipid bilayer envelope, and for example, the viral infection may be nephrotic hemorrhagic fever (epidemic hemorrhagic fever) caused by infection of a virus belonging to the family Bunyaviridae; a respiratory disease, such as runny nose or the like, caused by infection of a virus belonging to the family Coronaviridae; Hepatitis C caused by infection of a virus belonging to the family Flaviviridae; Hepatitis B caused by infection of a virus belonging to the family Hepadnaviridae; herpes zoster caused by infection of a virus belonging to the family Herpesviridae; influenza or influenza virus infection caused by infection of a virus belonging to the family Orthomyxoviridae; smallpox caused by infection of a virus belonging to the family Poxviridae; rabies or vesicular stomatitis caused by infection of a virus belonging to the family Rhabdoviridae; acquired immunodeficiency syndrome caused by infection of a virus belonging to the family Retroviridae; or the like, and as another example, the viral infection may be influenza or influenza virus infection caused by infection of an influenza virus belong to the family Orthomyxoviridae.

The nano-perforator included in the composition of the present invention may include one or more surface antigen receptors. For example, two or more receptors may be included in a single nano-perforator. In addition, the composition may include two or more nano-perforators including one or two or more different receptors.

The term “treatment” as used herein refers to an activity of improving or beneficially changing the symptom of an infection caused by viral infection.

The term “prevention” as used herein refers to prevention of a disease or disorder, or prevention of the onset, recurrence, or infection of one or more symptoms occurring due to a disease/disorder, and may include prophylactic treatment for potential candidates.

The composition of the present invention may be prepared in the form of a pharmaceutical composition for preventing or treating an inflammatory disease, which further includes a suitable carrier, excipient, or diluent commonly used in the preparation of pharmaceutical compositions, and the carrier may be a non-natural carrier. In particular, the pharmaceutical composition may be formulated into oral preparations such as powder, granules, tablets, capsules, suspensions, emulsions, syrups, aerosols, and the like, preparations for external application, suppositories, and sterile injection solutions, according to general methods. In the present invention, the composition may include one or more selected from the group consisting of various carriers, excipients, and diluents that may be included in pharmaceutical compositions.

An amount of the nano-perforator included in the pharmaceutical composition of the present invention is not particularly limited, but may range, for example, 0.0001 wt % to 10 wt %, for example, 0.01 wt % to 3 wt %, with respect to a total weight of the final composition.

The pharmaceutical composition of the present invention may be administered in a pharmaceutically effective amount. The term “pharmaceutically effective amount” as used herein refers to an amount sufficient to treat or prevent diseases at a reasonable benefit/risk ratio applicable to medical treatment or prevention, and an effective dosage level may be determined according to factors including the severity of disease, the activity of drugs, the age, body weight, health condition, and gender of patients, sensitivity of patients to drugs, the administration time, administration routes, and excretion rate of the used composition of the present invention, treatment periods, and drugs mixed or simultaneously used with the used composition of the present invention, and other factors well known in the medical field. The pharmaceutical composition of the present invention may be administered alone or administered in combination with a known agent for treating a viral infection. It is important to administer the pharmaceutical composition in the minimum amount that enables achievement of the maximum effects without side effects in consideration of all the above-described factors.

A dosage of the pharmaceutical composition of the present invention may be determined by one of ordinary skill in the art in consideration of the purpose of use, the severity of diseases, the age, body weight, gender, anamnesis of patients, the type of substance used as an active ingredient, or the like. For example, the pharmaceutical composition of the present invention may be administered in an amount of about 0.1 ng/kg to about 100 mg/kg, preferably 1 ng/kg to about 10 mg/kg per an adult, and the administration frequency of the composition of the present invention is not particularly limited, but the composition may be administered once a day or several times a day in multiple doses. The dosage is not intended to limit the scope of the present invention in any way.

The pharmaceutical composition for treating a viral infection according to the present invention may be administered via any general route as long as it enables the composition to reach target tissue. Administration routes of the pharmaceutical composition of the present invention include, but are not limited to, intraperitoneal administration, intravenous administration, intramuscular administration, subcutaneous administration, intradermal administration, oral administration, intranasal administration, intrapulmonary administration, intrarectal administration, and the like according to the purpose of use. However, since the nano-perforator can be denatured or destroyed by gastric acid in the case of oral administration, an oral composition has to be formulated such that an active ingredient is coated or is protected from decomposition in the stomach. In addition, the composition may be administered by an arbitrary device capable of delivering the active ingredient into target cells.

According to another embodiment of the present invention, there is provided a composition for inhibiting viral proliferation, which includes a nano-perforator including a lipid bilayer nanodisc and a membrane scaffold protein surrounding an outer circumferential surface of a lipid bilayer of the lipid bilayer nanodisc.

The foregoing description of the nano-perforator may be equally applied to the composition for inhibiting viral proliferation.

The inhibition of viral proliferation may be performed such that the nano-perforator perforates a virus envelope by binding thereto.

According to another embodiment of the present invention, there is provided a method of treating a viral infection, including administering a pharmaceutically effective amount of the pharmaceutical composition to an individual having the possibility of developing a viral infection caused by infection of a virus having a lipid bilayer envelope or having the viral infection.

The viral infection is the same as described above.

The term “individual” as used herein may encompass, without limitation, mammals including a human, a mouse, livestock, and the like, farmed fish, and the like that have the possibility of developing a viral infection caused by infection of a virus having a lipid bilayer envelope or having the viral infection.

According to another embodiment of the present invention, there is provided a method of screening for a receptor for a surface antigen of a target virus.

As described above, although the nano-perforator according to the present invention itself exhibits anti-viral activity against a virus having a lipid bilayer envelope, the nano-perforator including a receptor for a surface antigen for the virus on a lipid bilayer exhibits more effective anti-viral activity through a reaction between the receptor and the surface antigen. Thus, by reacting a nano-perforator including a receptor candidate material for a surface antigen of a target virus with the target virus, and then examining whether the nano-perforator exhibits anti-viral activity against the virus, it may be determined whether the candidate material can be used as the receptor for a surface antigen of a target virus.

In particular, the method of screening for a receptor for a surface antigen of a target virus, according to the present invention includes: (a) reacting a nano-perforator in which a receptor candidate material for a surface antigen of the target virus is inserted into a lipid bilayer, with the target virus; and (b) determining whether the nano-perforator exhibits anti-viral activity against the target virus.

In this regard, in process (b), the determination of whether the nano-perforator exhibits anti-viral activity against the target virus may be performed using, without being limited to, a known method selected from hemagglutination inhibition assay, RNA release analysis, plaque reduction assay, and the like, or a combination of these methods.

Advantageous Effects of Invention

When a nano-perforator according to the present invention is used, a disease caused by infection of a virus having a lipid bilayer envelope may be safely prevented or treated, and thus can be widely used in safe and effective treatment of viral infections.

BRIEF DESCRIPTION OF DRAWINGS

FIG. 1 is a schematic view illustrating the shape and structure of a lipid bilayer nano-perforator including a ganglioside according to the present invention.

FIGS. 2A and 2B are views and images showing results of analyzing the shape and structure of the lipid bilayer nano-perforator including a ganglioside according to the present invention through size exclusion chromatography, immunoblotting, dynamic light scattering, and an electron microscope.

FIG. 3 is a schematic view illustrating a mechanism for an effect of the nano-perforator including a ganglioside according to the present invention on inhibiting the proliferation of an influenza virus.

FIG. 4 is a set of images showing results of examining the effect of a nano-perforator including a ganglioside according to the present invention on inhibiting the proliferation of an influenza virus by disturbing the infection pathway of the influenza virus with which host cells were infected, through neutral red uptake inhibition assay.

FIG. 5A is a set of images and a graph showing analysis results of comparing the effect of a nano-perforator including a ganglioside according to the present invention on influenza virus-induced plaque formation with that of a liposome.

FIG. 5B is a set of images and a graph showing results of analyzing the effect of a nano-perforator including a ganglioside on influenza virus-induced plaque formation according to various concentrations.

FIG. 5C is a set of images and a graph showing results of analyzing the effect of a ganglioside included in a nano-perforator on influenza virus-induced plaque formation according to various concentrations.

FIG. 5D is a graph showing results of analyzing the effect of lipid composition in a nano-perforator on influenza virus-induced plaque formation.

FIG. 6 is a set of images showing the effect of a nano-perforator including a ganglioside according to the present invention on a reduction in cytopathic effect by acting on an influenza virus.

FIG. 7 is a set of a view and an image showing results of confirming whether a nano-perforator according to the present invention binds to an influenza virus in a ganglioside receptor-dependent manner, through immunoblotting.

FIG. 8 is a set of electron microscope images showing results of confirming whether a nano-perforator according to the present invention binds to an influenza virus in a ganglioside receptor-dependent manner.

FIG. 9A is a set of electrophoresis images and a graph showing RNA release analysis results obtained by reacting an influenza virus solution with various concentrations of a nano-perforator solution (NP or NPTG).

FIG. 9B is a set of electrophoresis images showing RNA release analysis results obtained by reacting an influenza virus solution with various concentrations of a liposome solution (LP or LPTG).

FIG. 9C is a set of electrophoresis images and a graph showing RNA release analysis results obtained by reacting an influenza virus solution with various concentrations of a nano-perforator solution (NP or NPTG) consisting of an apolipoprotein.

FIG. 10 is an immunoelectron microscope image showing results of confirming that a nano-perforator including a ganglioside according to the present invention fused with an influenza virus envelope to be released as an internal virus RNA-nucleoprotein complex.

FIG. 11 is a graph showing the effect of a nano-perforator including a ganglioside according to the present invention on erythrocyte hemolysis inhibition through fusion with an influenza virus envelope.

FIG. 12 is a set of microscope images showing results of confirming that a nano-perforator including a ganglioside according to the present invention bound to an influenza virus in a receptor-dependent manner and entered into cells, and could function in the cells.

FIG. 13 is a set of images showing the effect of a nano-perforator according to the present invention on a reduction in cytopathic effect by acting on a pseudorabies virus.

MODE OF INVENTION

Hereinafter, the present invention will be described in further detail with reference to the following examples. However, these examples are provided for illustrative purposes only and are not intended to limit the scope of the present invention.

Example 1: Preparation of MSP1E3D1 Protein-Containing Nano-Perforator (NP)

Example 1-1. Preparation of Nano-Perforator

As a lipid, a 25 mg/ml lipid solution, in which 1-palmitoyl-2-oleoyl-sn-glcero-3-phosphocholine (POPC) was dissolved in chloroform, was prepared. Subsequently, 152.02 μl of the 25 mg/ml POPC solution was transferred to a glass tube such that the concentration of lipid became 10 mM when dissolved with PBS supplemented with 0.5 ml of sodium cholate. Then, nitrogen gas was applied to the resulting solution, and the resulting solution was maintained in a vacuum for 4 hours to remove a solvent, thereby obtaining a lipid film. The obtained lipid film was hydrated with 0.5 ml of PBS supplemented with sodium cholate and sonicated at 55° C. for 15 minutes to obtain a lipid film-containing suspension in which the lipid film was pulverized. 160 μl of 250 μM MSP1E3D1 (SEQ ID NO: 12, molecular weight of 32.6 kDa) His-tagged at the N-terminus was added as a membrane scaffold protein to the obtained suspension, and the resulting suspension was treated with bio-beads (4° C., 12 hours) in the same amount (660 μl) as that of a whole mixed solution, thereby completing the preparation of a nano-perforator (NP) including the MSP1E3D1 protein through self-assembly.

Example 1-2. Preparation of Nano-Perforator Having Various Lipid Compositions A lipid bilayer nano-perforator having various lipid compositions was prepared using the same method as the preparation method of Example 1-1, except that a lipid solution including POPC, DOPS, and cholesterol in a molar ratio of 55:15:30 was used as a lipid.

Example 2: Preparation of ApoA-1 Protein-Containing Nano-Perforator (NP)

As a lipid, a 25 mg/ml lipid solution, in which 1-palmitoyl-2-oleoyl-sn-glcero-3-phosphocholine (POPC) was dissolved in chloroform, was prepared. Subsequently, 152.02 μl of the 25 mg/ml POPC solution was transferred to a glass tube such that the concentration of lipid became 10 mM when dissolved with PBS supplemented with 0.5 ml of sodium cholate. Then, nitrogen gas was applied to the resulting solution, and the resulting solution was maintained in a vacuum for 4 hours to remove a solvent, thereby obtaining a lipid film. The obtained lipid film was hydrated with 0.5 ml of PBS supplemented with sodium cholate and sonicated at 55° C. for 15 minutes to obtain a lipid film-containing suspension in which the lipid film was pulverized. 307.6 μl of 250 μM ApoA-1 (SEQ ID NO: 17, molecular weight of 29.8 kDa) tagged with histidine at the N-terminus was added as a membrane scaffold protein to the obtained suspension, and the resulting suspension was treated with bio-beads (4° C., 12 hours) in the same amount (807.6 μl) as that of a whole mixed solution, thereby completing the preparation of a nano-perforator including the ApoA-1 protein through self-assembly.

The ApoA-1 protein of SEQ ID NO: 17 used as the membrane scaffold protein is obtained by engineering the ApoA-1 protein of SEQ ID NO: 1, and in the amino acid sequence of SEQ ID NO: 17, amino acids 2 to 7 from the N-terminus are His-tagged, amino acids 9 to 14 are thrombin cleavage sites, and amino acids 16 to 19 are ASP-PRO acid labile bonds.

Example 3. Preparation of Ganglioside-Containing Nano-Perforator (NPTG)

Example 3-1. Preparation of Ganglioside-Containing Nano-Perforator

A ganglioside-containing lipid bilayer nano-perforator (NPTG) was prepared in the same manner as in Example 1-1, except that POPC in chloroform and total gangliosides (available from Avanti Polar Lipids, Inc.) including GM3, GM2, GM1, GD1a, GD1b, and GT1b were dissolved so as to have a molar ratio of 85:15.

Example 3-2. Preparation of Nano-Perforators Including Various Concentrations of Ganglioside Ganglioside-containing lipid bilayer nano-perforators (NPTG) were prepared in the same manner as in Example 1-1, except that POPC in chloroform and total gangliosides (available from Avanti Polar Lipids, Inc.) including GM3, GM2, GM1, GD1a, GD1b, and GT1b were dissolved so as to have each of molar ratios of 100:0, 95:5, 85:15, 80:20, 70:30, 60:40, and 50:50.

Example 3-3. Preparation of GD1a Ganglioside-Containing Nano-Perforator

A ganglioside-containing lipid bilayer nano-perforator (NPGD1a) was prepared in the same manner as in Example 1-1, except that POPC in chloroform and the GD1a ganglioside (available from Enzo Life Sciences, Inc.) were dissolved so as to have a molar ratio of 85:15.

Example 3-4. Preparation of Ganglioside-Containing Nano-Perforator Having Various Lipid Compositions A ganglioside-containing lipid bilayer nano-perforator (NPTG) having various lipid compositions was prepared in the same manner as in Example 1-1, except that POPC, DOPS, cholesterol, in chloroform, and total gangliosides including GM3, GM2, GM1, GD1a, GD1b, and GT1b (available from Avanti Polar Lipids, Inc.) were dissolved so as to have a molar ratio of 40:15:30:15.

Example 3-5. Preparation of ApoA-1 Protein- and Ganglioside-Containing Nano-Perforator A ganglioside-containing lipid bilayer nano-perforator (NPTG) was prepared in the same manner as in Example 1-1, except that POPC in chloroform and total gangliosides including GM3, GM2, GM1, GD1a, GD1b, and GT1b (available from Avanti Polar Lipids, Inc.) were dissolved so as to have a molar ratio of 85:15.

Example 4. Identification of Structures of Nano-Perforators

The sizes and shapes of the nano-perforators prepared according to Examples 1-1, 2, 3-1, and 3-5 were identified through size exclusion chromatography, immunoblotting, dynamic light scattering, and an electron microscope, and the results thereof are illustrated in FIGS. 2A and 2B.

As a result of identifying the sizes and shapes of the prepared nano-perforators, it was confirmed that each nano-perforator had a diameter of about 10 nm, included a lipid bilayer therein, and had a structure in which an outer circumferential surface of the lipid bilayer having a disc shape was surrounded by the MSP1E3D1 protein (see FIG. 2A, the nano-perforator NP of Example 1-1 and the nano-perforator NPTG of Example 3-1) or ApoA-I (see FIG. 2B, the nano-perforator NP of Example 2 and the nano-perforator NPTG of Example 3-5).

In addition, it was confirmed that in the case of the ganglioside-inserted nano-perforators NPTG of Examples 3-1 and 3-5, the gangliosides were inserted into a disc surface of the lipid bilayer.

Example 5: Viral Proliferation Inhibitory Activity of Nano-Perforator

Example 5-1. Neutral Red Uptake Inhibition Assay

Generally, when a cell is treated with a neutral red dye, the dye permeates into a cell membrane by non-ionic passive diffusion and is collected in a lysosome, and the absorption of neutral red depends on the ability of cells to maintain a pH gradient through ATP production. When the NPTG is added and allowed to react under conditions in which cells are treated with a virus to the extent that does not allow the cells to absorb neutral red, the nano-perforator is fused with an envelope of an influenza virus to render a structure of the virus envelope unstable, and RNA inside the virus is released to the outside of the envelope due to the unstable envelope. When the cells have absorbed neutral red dye, it may be analyzed that the cell survival rate is increased by the effect of NPTG.

To confirm whether the nano-perforators of Examples 1-1 and 3-1 increase cell survival rates by acting on an influenza virus, a neutral red uptake inhibition assay was performed.

On the day before an experiment, 200 μl of half of MDCK cells of a completely filled T-75 flask was dispensed into each well of a 96-well plate, and on the day of the experiment, the cells were washed twice with PBS after removing the cell medium. Then, the cells were infected by treating each well with 50 H3N2 Sydney viruses (purchased from NIBSC) (50 PFU) for 45 minutes and unbound viruses were removed, and then 200 μl of each of media diluted with trypsin and various concentrations (1,000 nM, 500 nM, 250 nM, 125 nM, 62.5 nM, 31.25 nM, and 15.625 nM) of the nano-perforator of Example 1-1 or the nano-perforator of Example 3-1 was dispensed into each well. After incubation at 37° C. for 48 hours, the medium was removed, and each well was treated with 100 μl of 40 g/ml of a neutral red dye and allowed to react for 2 hours. After the reaction was completed, the dye was removed, and the cells were washed once with 200 μl of PBS. Thereafter, each well was treated with 200 μl of a neutral red destain solution (50% ethanol, 49% distilled water, and 1% acetic acid), and then absorbance at 540 nm was measured (see FIG. 4). As controls, a condition without virus treatment (cell only), a condition including only virus treatment without Tamiflu treatment ((−) control), and a condition including treatment with both a virus and Tamiflu ((+) control) were set.

FIG. 4 is a set of images showing the effect of a nano-perforator including a ganglioside, according to the present invention on cell survival rate by acting on an influenza virus, and it was confirmed therefrom that both the ganglioside-containing nano-perforator (NPTG) and the ganglioside-free nano-perforator (NP) exhibited a cell survival effect similar to that of Tamiflu, which is a positive control. That is, it was confirmed that NP and NPTG exhibited very strong virus inhibitory effects even at low concentrations, and in particular, NPTG exhibited a significantly greater anti-viral effect than NP. In addition, it can be confirmed that in consideration of no difference in anti-viral effect between NP or NPTG and Tamiflu as a control, the nano-perforators are effective as anti-viral agents.

Example 5-2. Plaque Reduction Assay

A plaque refers to a void formed by infecting a host cell with a virus and covering a culture plate with an agarose-media mixed solution, not allowing generated viruses to widely spread and killing only neighboring cells by infection. Since plaque formation is inhibited by inhibition of the activity of the virus, whether the level of plaque formation was reduced was confirmed by examining whether NP of Example 1, NPTG of Example 3, and as controls, a liposome (LP) and a liposome including 15% of a ganglioside (LPTG) exhibited anti-viral activity by fusing with an influenza virus envelope.

The liposome and/or the ganglioside-containing liposome, which were used as controls, were prepared as follows.

A phosphatidylcholine (PC) alone (liposome, LP) or PC and a ganglioside in a molar ratio of 85:15 (ganglioside-containing liposome, LPTG) was dissolved in chloroform to prepare a lipid solution, and the lipid solution was added to a glass tube and nitrogen gas was allowed to flow thereinto, thereby forming a lipid film such that the concentration of lipid became 10 mM when dissolved with 200 μl of PBS, and the lipid film was maintained in a vacuum for 12 hours to 16 hours to remove the remaining organic solvent. Subsequently, the lipid film was treated with 0.2 ml of PBS and dissolved by vortexing to obtain multi-lamellar liposomes having various sizes, and the resulting solution was repeatedly frozen and thawed with liquid nitrogen in a water bath at 42° C. a minimum of five times to obtain uni-lamellar liposomes having various sizes. Thereafter, extrusion was performed to make the size constant. The extrusion process was performed by placing a membrane having a size of 100 nm between two glass syringes (0.25 ml syringe) and reciprocating the obtained liposomes through the membrane a minimum of 10 times by using the syringes, to prepare a liposome having a spherical shape with a diameter of about 100 nm to about 120 nm and a single membrane, followed by storage at 4° C.

For plaque reduction assay, MDCK cells were inoculated into each well of a 6-well plate at a density of $1\times10^6$ cells and cultured, and after 24 hours, the cultured cells were washed twice with PBS. 0.5 ml of a solution of 100 PFU A/Puerto Ri co/8/1934 H1N1 influenza virus (purchased from NIBSC) was added to the washed cells, and the cells were allowed to react at room temperature for 1 hour while being continuously shaken. Subsequently, the culture solution was removed from each well, and 3 ml of an agarose solution (HEPES 25 mM, sodium bicarbonate 22 mM, DMEM, 1% agarose, pH 7.4) including various concentrations (4 μM, 20 μM, 100 μM, or 500 μM) of each of the nano-perforators of Examples 1-1, 1-2, 3-1, 3-2, and 3-4 and the liposome (LP) and the ganglioside-containing liposome (LPTG), which were used as controls, was added to the cells, followed by solidification at room temperature for 1 hour, and the cells were incubated in a $CO_2$ incubator at 37° C. for 3 hours, and the levels of formed plaques were compared with one another. At this time, an experimental group, in which an agarose solution not including the nano-perforators or liposomes was used, was used as a control. The results thereof are illustrated in FIGS. 5A, 5B, 5C, and 5D.

FIG. 5A is a set of images and a graph showing analysis results of comparing the effect of a nano-perforator according to the present invention on influenza virus-induced plaque formation with that of a liposome. As illustrated in FIG. 5A, it was confirmed that while a control (Ctrl) exhibited overall plaque formation due to an influenza virus, both the receptor-containing nano-perforator of Example 3-1 and the receptor-free nano-perforator of Example 1-1 exhibited a reduced number and size of plaques. It was confirmed that such effects were much stronger than those of the liposome (LP) and the receptor-containing liposome (LPTG) treated at the same concentration. Compared with LPTG, which exhibited some effect on inhibition of the size of plaques, it was confirmed that NPTG inhibited the size of plaques by approximately 80% and also inhibited the number of plaques by about 20%. From these results, it was confirmed that the nano-perforator was a very crucial factor in exhibiting anti-viral efficacy. It was additionally confirmed that although the nano-perforator (NP) of Example 1-1 not including a ganglioside exhibited a weaker anti-viral effect than the ganglioside-containing nano-perforator (NPTG) of Example 3-1, the nano-perforator of Example 1-1 exhibited a reduced number and size of plaques upon treatment at a high concentration.

FIG. 5B is a set of images and a graph showing results of analyzing the effect of a nano-perforator including a ganglioside on influenza virus-induced plaque formation. As illustrated in FIG. 5B, it was confirmed that unlike the case of a control (No NP) that exhibited overall plaque formation, the ganglioside-containing nano-perforator (NPTG) of Example 3-1 exhibited a reduced number and size of plaques in a concentration-dependent manner. In particular, it was confirmed that the NPTG of Example 3-1 inhibited the size of plaques by 70% and the number of plaques by about 20% even at a concentration of 40 nM, and reduced the size of plaques by about 90% and the number of plaques by 50% or more at 200 nM, and form these results, it was confirmed that the nano-perforator exhibited a considerable viral activity inhibitory effect even at a low concentration.

FIG. 5C is a set of images and a graph showing results of analyzing the effect of concentration of a receptor in the nano-perforator of Example 3-2 on influenza virus-induced plaque formation. As illustrated in FIG. 5C, it was confirmed that the greater the amount of a ganglioside at the same concentration of the nano-perforator, the much smaller the size and number of plaques. In particular, it was confirmed that, compared to the control, the size and number of plaques were inhibited by 50% and about 30%, respectively, even when the molar proportion of the ganglioside was merely 5%. It was confirmed that such effects were dependent on the concentration of the included ganglioside, and when the molar proportion thereof is 50%, the nano-perforator exhibited the greatest effect, i.e., a reduction in the size of plaques by 90% or more and the number of plaques by about 80%, and from these results, it was finally confirmed that ganglioside had to be included at a minimum of 15% or more to enhance an anti-viral effect.

FIG. 5D is a graph showing results of analyzing the effects of a control treated only with a virus and the nano-perforators of Examples 3-1 and 3-4 on influenza virus-induced plaque formation. As illustrated in FIG. 5D, it was confirmed that compared to the nano-perforator of Example 3-1 consisting simply of only POPC as a lipid other than the receptor under conditions upon treatment with the same concentration of nano-perforator, the nano-perforator of Example 3-4 further including POPC, DOPS, and/or cholesterol exhibited a more excellent anti-viral effect. In addition, it was confirmed that as in the above-described other experimental results, due to this effect, the number of plaques could also be significantly reduced unlike the case of mainly inhibiting only the size of plaques. This effect is thought to be due to the effects of DOPS and cholesterol, which are lipids known to help membrane fusion, since the nano-perforator plays a major role in membrane fusion.

Taken the results of Examples 5-1 and 5-2 together, it can be seen that the nano-perforator according to the present invention exhibits, at a high concentration, anti-viral activity against an influenza virus even though not including a ganglioside, and the ganglioside-containing nano-perforator exhibits significantly excellent anti-viral activity.

Example 6: Cytopathic Effect Reduction Assay

A cytopathic effect refers to a phenomenon in which a host cell having grown on a plate is infected with a virus, and when viral replication sufficiently occurs, the attached host cell dies, undergoes a morphological change and eventually floats. When the activity of the virus is inhibited, the cytopathic effect will be reduced, and thus through this, it was examined whether the NPTG of Example 3 exhibited anti-viral activity through fusion with an influenza virus envelope.

Figure 6:
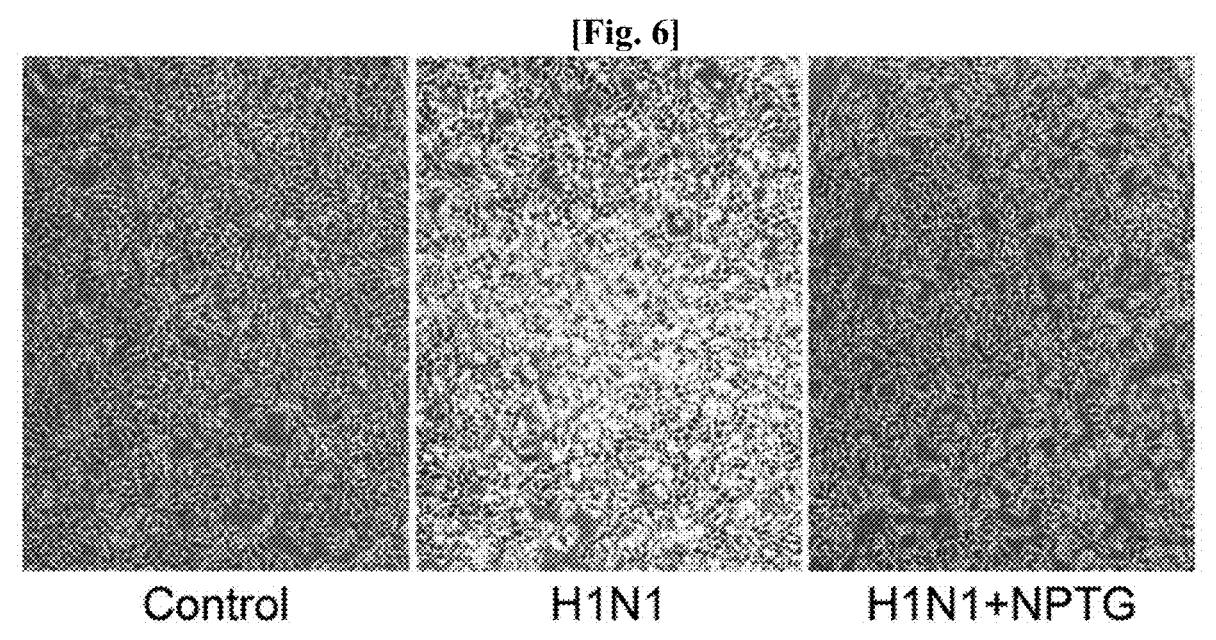

In particular, MDCK cells were inoculated into each well of a 12-well plate at a density of $1.5\times10^5$ cells and cultured, and after 24 hours, the cultured cells were washed twice with PBS. $6\times10^5$ PFU/ml of an A/Puerto Rico/8/1934 H1N1 virus (purchased from NIBSC) inoculant was prepared using a FBS-free incomplete MEM medium and 0.25 ml of the virus solution was added to the washed MDCK cells, and the cells were allowed to react at room temperature for 1 hour while being continuously shaken. Subsequently, the culture solution was removed from each well and 1 ml of a 500 nM solution including the nano-perforator (NPTG) of Example 3-1 (MEM medium containing 1× antibiotics, pH 7.4) was added to the cells, and the cells were incubated at 37° C. for 1 hour, and levels of inhibition of the cytopathic effect were compared with one another. At this time, a condition not including the nano-perforator and including only treatment with a virus and a condition including only cells not treated with a virus were used as controls. The results thereof are illustrated in FIG. 6.

FIG. 6 is a set of images showing results of analyzing the effect of the ganglioside-containing nano-perforator (NPTG) of Example 3-1 on an influenza virus-induced cytopathic effect. As illustrated in FIG. 6, it was confirmed that while healthy MDCK cells not infected with a virus were shown in the control, the cytopathic effect was exhibited in a condition in which MDCK cells were infected with a virus (H1N1), resulting in cell shape changes and cell death and detachment. Under the same conditions, when 1 μM of NPTG was treated, no virus-induced cytopathic effect was observed and healthy MDCK cells were maintained well, and from these results, it was confirmed that NPTG was highly effective in inhibiting viral infection.

Example 7: Nano-Perforator Binding Test

Example 7-1: Bead Binding Assay

The function of the nano-perforator as an entry inhibitor was examined using a His-tag attached to the N-terminus of the nano-perforator protein. When NP or NPTG is treated with agarose beads with nickel ions bound thereto, strong bonding is possible due to the binding affinity between divalent cations and histidine. Subsequently, when the resulting structure is treated with an influenza virus and a reaction therebetween is allowed to occur fully, the virus may bind only to an NPTG solution via hemagglutinin and finally, the virus is present in an eluate obtained by treatment with an elution solution containing a high concentration of imidazole and may be identified by immunoblotting.

By using the above-described principle, it was examined whether a nano-perforator is capable of binding to an influenza virus in a ganglioside-dependent manner by using the NP of Example 1-1 or the NPTG of Example 3-1 and whether the nano-perforator acts as an entry inhibitor, which is a primary inhibitory function.

In particular, 50 μl of nickel agarose beads were washed three times with a washing solution (PBS containing 5 mM imidazole, pH 7.4), and then treated with 200 μl of 50 μM of the NP of Example 1-1 or the NPTG of Example 3-1, which was previously prepared, and allowed to react at 4° C. for 2 hours. After the reaction was completed, the resulting complex was washed once with the same washing solution to remove unbound nano-perforators, treated with 0.8 ml of $1\times10^8$ PFU/ml of the prepared A/Puerto Rico/8/1934 H1N1 influenza virus (purchased from NIBSC), and then allowed to react at 4° C. for 2 hours. Thereafter, the resulting complex was washed a total of three times with the same washing solution to remove unbound viruses, followed by treatment with 0.1 ml of an elution solution containing a high concentration of imidazole (PBS containing 500 mM imidazole, pH 7.4) to obtain an eluate. To confirm whether the virus is present in the elate, immunoblotting was performed using a mouse primary antibody against virus hemagglutinin and a rabbit secondary antibody capable of binding thereto. The results thereof are illustrated in FIG. 7.

FIG. 7 is a set of a view and an image showing analysis results of confirming whether a nano-perforator is able to act as an entry inhibitor by binding to influenza virus hemagglutinin in a manner dependent on a ganglioside, which is a receptor. The H1N1 virus was used in combination as a positive control for immunoblotting. Unlike the ganglioside-free nano-perforator (NP), immunoblotting was confirmed only under a condition of the ganglioside being contained in the nano-perforator (NPTG). This suggests that the virus can bind to the ganglioside as a receptor via hemagglutinin and NPTG eventually may act as an entry inhibitor, which is a primary inhibitory function.

Example 7-2: Transmission Electron Microscopy

As another method for confirming whether the nano-perforator binds to an influenza virus in a ganglioside-dependent manner, transmission electron microscopy was performed. An electron microscope is an apparatus that creates an enlarged image of an object using electrons instead of light and allows you to see small objects such as viruses and nano-perforators, which are not observed using an optical microscope. When transmission electron microscopy was performed in a state in which a virus was mixed with NP or NPTG, the NP was present separately from the virus since it had no receptor, but it was expected that NPTG was present in a state of being attached around the virus since it was capable of binding to hemagglutinin due to the presence of a receptor, i.e., a ganglioside. Thus, analysis was performed to confirm whether the NP of Example 1-1 or the NPTG of Example 3-1 is capable of binding to an influenza virus envelope.

In particular, 16.6 μl of 40 μM of the NP of Example 1-1 or the NPTG of Example 3-1 was mixed with $1\times10^8$ PFU/ml of an A/Puerto Rico/8/1934 H1N1 influenza virus (purchased from NIBSC) and was allowed to react at room temperature for 1 hour for binding therebetween. Subsequently, 20 μl of the mixed solution was dropped on each grid used in an electron microscope and maintained for 1 minute to allow samples to bind to the grid. The unbound samples were absorbed using 3M paper, and then each grid was washed twice with water, followed by staining with 2% uranyl acetate for 1 minute, and the remaining dye was absorbed by 3M paper. Thereafter, a transmission electron microscope Libra 120 was used for microscopic analysis. The results thereof are illustrated in FIG. 8.

Figure 8:
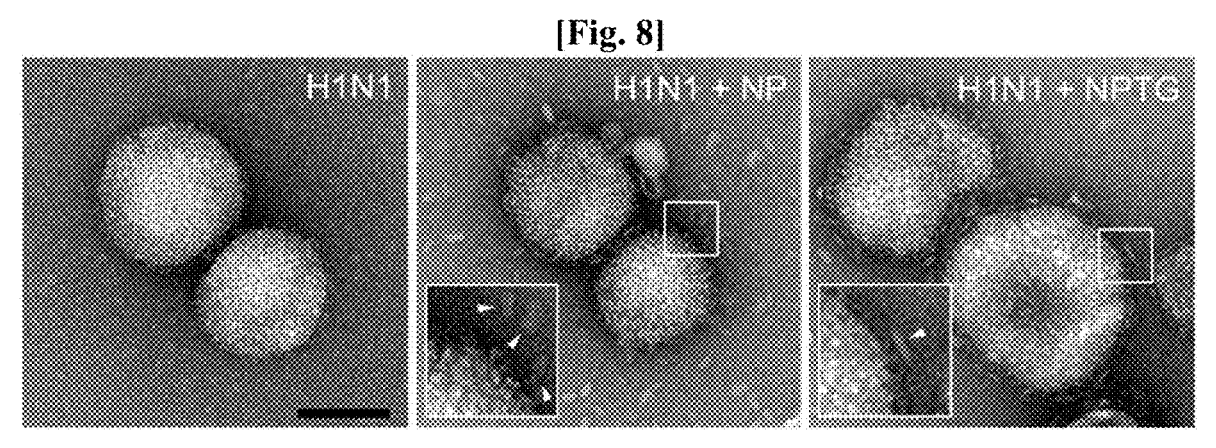

FIG. 8 is a set of images showing analysis results of confirming whether a nano-perforator is able to function as an entry inhibitor by binding to influenza virus hemagglutinin in a manner dependent on a ganglioside, which is a receptor. In the control treated only with the virus (H1N1), it was confirmed that the virus had a diameter of about 100 nm to about 200 nm, and it was confirmed that unlike the case of a H1N1+NP (Example 1-1) condition in which the nano-perforator was present separately from the virus, the nano-perforators surrounded the virus under a H1N1+NPTG (Example 3-1) condition. Similar to Example 7-1, gangliosides, which are receptors, were bound to hemagglutinins of an outer portion of the virus, from which it was confirmed that the nano-perforators were present in a state of being bound around the virus. Through this, it was confirmed that the ganglioside-containing nano-perforator could sufficiently function as an entry inhibitor as in Example 7-1.

Example 8: RNA Release Assay

When an influenza virus is treated with the nano-perforator of the present invention, the nano-perforator is fused with an envelope of the influenza virus, and a structure of the virus envelope is rendered unstable, and RNA inside the virus is released to the outside of the virus due to the unstable envelope. It was examined whether each of the nano-perforators of Examples 1-1, 2, 3-1, and 3-5 (NP or NPTG) was fused with the influenza virus envelope by using Centricon® through which while RNA having a smaller size of that of pores thereof is allowed to be filtered, virus particles having a greater size than that of the pores is not allowed to be filtered.

In particular, $5\times10^7$ PFU/ml of an A/Puerto Rico/8/1934 H1N1 influenza virus (purchased from NIBSC) solution was mixed with various concentrations (1.3 μM, 13 μM, 130 μM, or 1,300 μM) of each of the nano-perforators of Examples 1-1, 2, 3-1, and 3-5 so as to have a total volume of 200 μl, and then the resulting mixture was allowed to react at 37° C. for 0.5 hours, and pH 5.0 was maintained using 8.66 μl of 0.1 M citric acid, followed by a reaction therebetween again for 15 minutes. The reaction-completed samples were added to Centricon® to perform centrifugation (13,000 rpm, 5 min, 4° C.), thereby obtaining an unfiltered sample (R, retentate) and a filtered sample (F, filtrate). At this time, a condition in which only an influenza virus solution (V) was used, was used as a control.

Each sample was subjected to reverse transcription PCR (a mixed solution of 5 μl of a template, 1 μl of a sense primer (M gene), and 7.4 μl of water was allowed to react at 70° C. for 10 minutes, and then 4 μl of 5× reverse transcription buffer, 1.6 μl of dNTP, and 1 μl of RTase were added thereto and allowed to react at 42° C. for 1 hour and 70° C. for 10 minutes) to obtain cDNA corresponding to RNA included in each sample. Subsequently, PCR (a mixed solution of 5 μl of a template, 10 μl of water, 0.5 μl of each of sense/antisense primers (M gene), and 4 μl of 5× rTaq DNA polymerase was prepared and first allowed to react at 95° C. for 3 minutes, and then a total of 30 cycles of three consecutive reactions of 95° C., 10 seconds/56° C., 10 seconds/72° C., 10 seconds were performed, finally followed by a reaction at 72° C. for 5 minutes) was performed on each sample using the obtained cDNA as a template, and the PCR products were identified by electrophoresis (see FIG. 9A). Meanwhile, the same experiment was carried out using the LP or ganglioside-containing LPTG of Example 5-2 as comparative groups instead of the nano-perforators, and then the results thereof were confirmed (see FIG. 9B).

FIG. 9A is a set of electrophoresis images showing RNA release analysis results obtained by reacting an influenza virus solution with various concentrations of the NP solution of Example 1-1 or the NPTG solution of Example 3-1. FIG. 9B is a set of electrophoresis images showing RNA release analysis results obtained by reacting an influenza virus solution with various concentrations of an LP or LPTG solution. FIG. 9C is a set of electrophoresis images showing RNA release analysis results obtained by reacting an influenza virus solution with various concentrations of the NP solution of Example 2 or the NPTG solution of Example 3-5.

As illustrated in FIG. 9A, while RNA was not detected in the sample (F) filtered through Centricon® in the control not treated with the nano-perforator (V), RNA was detected in the sample (F) filtered through Centricon® in the experimental groups treated with the nano-perforator. In particular, when the ganglioside-free nano-perforator (NP) was added at a concentration of 130 μM or more to an influenza virus solution, RNA was detected in the sample (F) filtered through Centricon®, but in the case of the ganglioside-containing nano-perforator (NPTG) added even at a concentration of 1.3 μM, RNA was detected in the sample (F) filtered through Centricon®.

However, as illustrated in FIG. 9B, it was confirmed that when the influenza virus solution was reacted with various concentrations of the LP or LPTG solution, RNA was not detected in the sample (F) filtered through Centricon® in any case.

In addition, as illustrated in FIG. 9C, it was confirmed that when the influenza virus solution was reacted with various concentrations of each of the nano-perforators consisting of ApoA-1 that were prepared according to Examples 2 and 3-5, the release of internal virus RNA was induced through membrane fusion with the virus envelope at a concentration of the nano-perforator of 1 μM or more and the RNA was detectable. In the case of ApoA-1-based nano-perforators having a small diameter of about 10 nm, it was confirmed that they sufficiently damaged the virus envelope even without the receptor, thus exhibiting an effect.

Example 9: Analysis of Release of RNA-Nucleoprotein Complex

Immunoelectron microscopy is a method of detecting antigen distribution using an immune response through an antibody, and as a secondary antibody used, a metal having a high electron density such as gold (Au) particles, ferritin, or the like, or an enzyme such as peroxidase or the like is widely used. Under conditions (pH 5.0) in which the nano-perforator exhibits anti-viral activity by being fused with a virus envelope, a virus RNA-nucleoprotein complex is released to the outside of the virus. At this time, to detect the nucleoprotein, immunoelectron microscopy was performed using an antibody for recognizing the nucleoprotein as an antigen, through which whether RNA is actually released to the outside may be directly confirmed visually.

Using the above-described principle, it was examined whether the NPTG of Example 3-1 exhibited anti-viral activity through fusion to the influenza virus envelope.

In particular, a parafilm was placed on the bottom and 0.1 ml of a mixed solution of an A/Puerto Rico/8/1934 H1N1 virus (purchased from NIBSC) and the NPTG of Example 3-1 was dropped thereon, and a grid for an electron microscope was mounted thereon and maintained at room temperature for 20 minutes, the pH of the mixed solution was reduced to 5.0, and then the mixed solution was maintained further for 10 minutes. Subsequently, the grid was washed with PBS once for 2 minutes and for blocking, treated with a PBS solution containing 1% BSA at room temperature for 30 minutes. Then, 50 g/ml of a primary antibody capable of binding to the virus nucleoprotein was prepared using PBS containing 1% BSA and the grid was treated therewith to allow a reaction to occur therebetween at room temperature for 1 hour. Thereafter, the grid was washed with PBS containing 1% BSA a total of twice each for 3 minutes, a gold-labeled secondary antibody capable of recognizing and binding to the primary antibody was diluted to 1:50, and the grid was treated with the secondary antibody and maintained at room temperature for 45 minutes. Thereafter, the grid was washed a total of three times with PBS, treated with 4% formaldehyde prepared using PBS at room temperature for 10 minutes for fixation, and then successively washed twice with distilled water, and staining was performed using 2% uranyl acetate according to the method described above in the transmission electron microscopy and electron microscope manipulation and analysis were performed on the sample. The results thereof are illustrated in FIG. 10.

Figure 10:
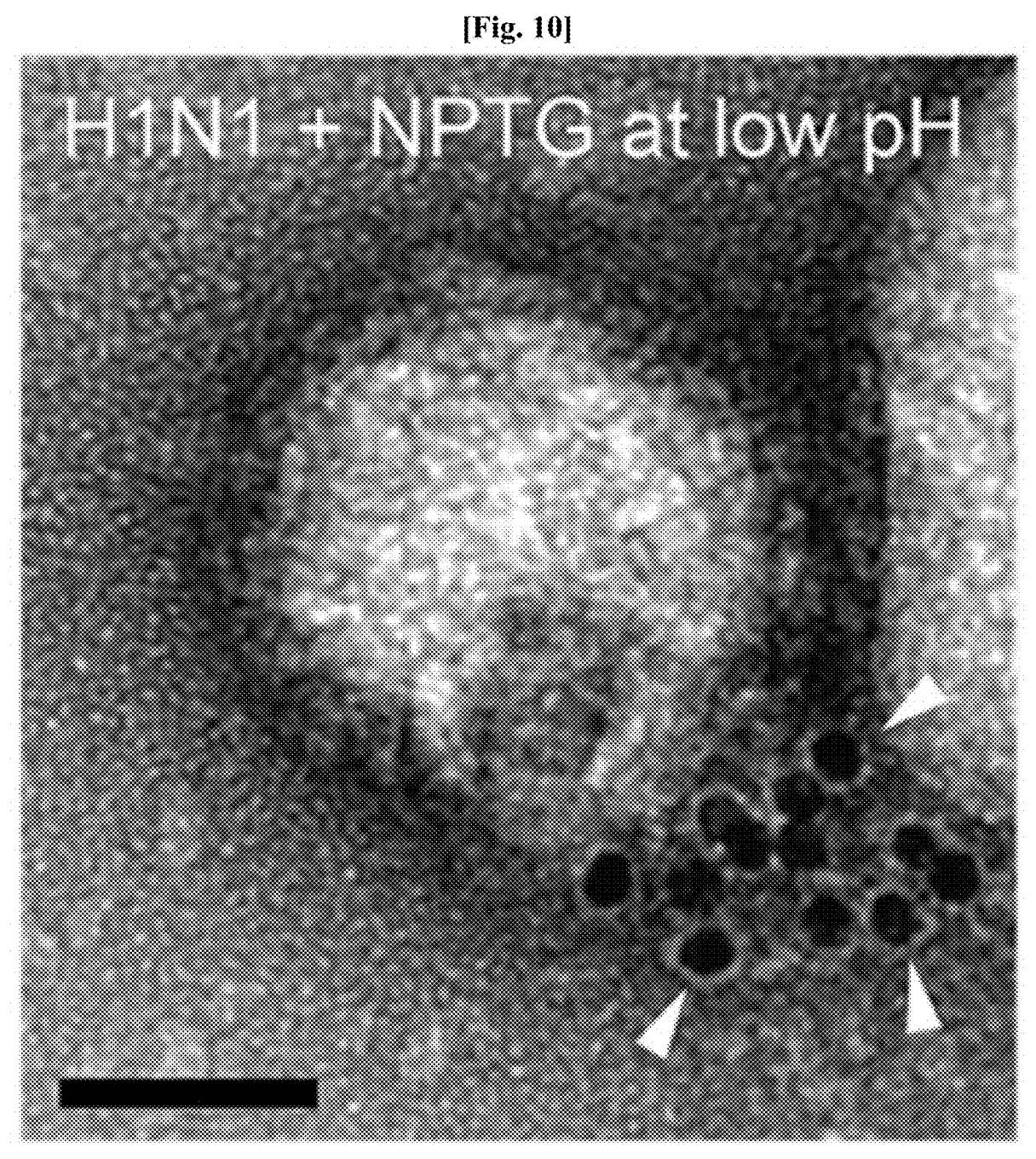

FIG. 10 is an immunoelectron microscope image showing results of confirming that RNA inside the virus was actually released to the outside as a result of fusion of the ganglioside-containing nano-perforator of Example 3-1 to an influenza virus envelope at a low pH. It was confirmed that when a virus was treated with the nano-perforator and pH was reduced, an envelope of the virus was damaged, and thus the virus RNA-nucleoprotein complex was released to the outside and detectable as black spots by an antibody capable of binding to the complex. Through this, it was confirmed that the nano-perforator physically damaged the virus envelope at a low pH of an intracellular liposome to allow RNA inside the virus to be released to the outside, thereby inhibiting the progression of viral infection.

Example 10: Hemolysis Inhibition Assay

Hemolysis inhibition by the nano-perforator means competitive inhibition of membrane fusion between a virus and a red blood cell, and it may be considered that the nano-perforator actually competitively inhibits fusion between a viral membrane and an endosomal membrane in a cell.

It was examined using the above-described principle whether the nano-perforators of Examples 1-1 and 3-1 (NP or NPTG), and the nano-perforator (NPGD1a) of Example 3-3 prepared using GD1a ganglioside, which is known to more strongly bind to the used virus, inhibited hemolysis through fusion with the influenza virus envelope.

In particular, the NP of Example 1-1, the NPTG of Example 3-1, or the NPGD1a of Example 3-3 was subjected to serial dilution using PBS to ½ and 100 μl of each diluted nano-perforator was prepared in each well of a 96-well plate, and each well was treated with the same amount of an A/Puerto Rico/8/1934 H1N1 virus (purchased from NIBSC) and allowed to react at 37° C. for 1 hour. Subsequently, 2% chicken red blood cells prepared in the same amount and diluted with PBS was further added to each well, and the resulting solution was further allowed to react at 37° C. for 10 minutes. Then, the pH of the solution was reduced to 5.0 using 1N acetic acid and the resulting solution was centrifuged (at 400×g; 8 minutes; 4° C.) to remove the chicken red blood cells. 300 μl of the supernatant was collected and transferred to a new 96-well plate, and absorbance at 540 nm was analyzed. The results thereof are illustrated in FIG. 11.

FIG. 11 illustrates analysis results of levels of inhibition of influenza virus-induced erythrocytic hemolysis according to various concentrations. It was confirmed that while the ganglioside-free NP of Example 1-1 did not inhibit erythrocytic hemolysis at all within the tested concentration ranges, the ganglioside-containing nano-perforator (NPTG of Example 3-1 or NPGD1a of Example 3-3) inhibited erythrocytic hemolysis in a concentration-dependent manner. In particular, it was confirmed that the NPGD1a of Example 3-3 exhibited much stronger inhibitory effect than that of the NPTG of Example 3-1, and this is considered due to the fact that the GD1a ganglioside binds to a virus more strongly. From these results, it was confirmed that during viral infection, the nano-perforator had a competitive edge over an endosomal membrane at a low pH of an intracellular lysosome and physically damaged the virus envelope, thereby inhibiting the viral infection.

Example 11: Test for Intracellular Penetration of Nano-Perforator

Confocal microscopic analysis may be used to confirm whether a ganglioside-containing nano-perforator (NPTG or NPGD1a) actually enters into a cell along with a virus and inhibits an infection process.

By using the above-described principle, it was examined whether the nano-perforator of Example 1-1 (NP) or Example 3-1 (NPTG) and additionally, the nano-perforator (NPGD1a) of Example 3-3 prepared using the GD1a ganglioside, which is known to bind more strongly to the used virus, binds to the envelope of an invading influenza virus and enters into a cell along therewith.

In particular, to label the membrane of an A/PR/8/34 influenza virus (purchased from NIBSC) used in an experiment with SP-DiOC18, which is a fluorescent dye with lipid affinity, a virus was mixed with SP-DiOC18 and allowed to react at room temperature for a minimum of 12 hours. Subsequently, a PD-10 desalting column was used to remove the dye that was not inserted into the virus membrane, and finally, a fluorescence-labeled virus was obtained and refrigerated until use. At the same time, for fluorescence detection, nano-perforators were prepared by adding 1% of Liss-Rhod phosphatidylethanolamine, which is a fluorescent lipid, to the nano-perforators of Examples 1-1, 3-1, and 3-3 in the lipid film formation process. The prepared virus and each prepared nano-perforator were previously mixed and allowed to react in a refrigerator for 2 hours, and prepared A549 cells prepared in a 100 mm cell culture dish on the previous day were treated with the mixed solution and infected at 37° C. for 2 hours. Thereafter, the cells were fixed with 4% of formaldehyde for 15 minutes. The cells were then washed with PBS and mounted with a Gold antifade mountant, and images were acquired using a Carl Zeiss LSM confocal microscope and analyzed. The results thereof are illustrated in FIG. 12.

FIG. 12 is a set of microscope images showing results of confirming that nano-perforators treated together with an influenza virus actually entered into a cell along with the virus when the virus infiltrated into the cell.

It was confirmed that A/PR/8/34, which is a virus used in the experiment, penetrated into a cell by endocytosis and was detected as dots by labeled fluorescence, and it was also confirmed that the nano-perforators labeled with the fluorescence lipid (NP of Example 1-1, NPTG of Example 3-1, or NPGD1a of Example 3-3) entered into a cell and appeared as dots. In particular, it was confirmed that while the fluorescence dots shown by the NP of Example 1-1 did not overlap with those of the virus, overlapping dots were present between the virus and the NPTG of Example 3-1 or the NPGD1a of Example 3-3. This confirms that the nano-perforators bind to a virus in a receptor-dependent manner and actually enter satisfactorily into a cell. Such a level was much higher in the NPGD1a of Example 3-3 than in the NPTG of Example 3-1, and in the case of NPGD1a of Example 3-3, the fluorescence dots overlapped with almost all the fluorescence dots of the virus, from which it was further confirmed that this resulted from much stronger binding of the GD1a ganglioside to the hemagglutinin of the virus.

Example 12: Cytopathic Effect Reduction Assay

To confirm whether the nano-perforator of Example 1-1 exhibits anti-viral activity by being fused with a virus envelope even when infected with pseudorabies virus (PRV), a cytopathic effect reduction assay was performed.

The cytopathic effect reduction assay was performed in the same manner as in Example 6, except that HeLa cells were infected with PRV instead of MDCK cells being infected with an influenza virus, and the results thereof are illustrated in FIG. 13.

FIG. 13 is a set of images showing results of analyzing the effect of the nano-perforator (NP) of Example 1-1 on a PRV-induced cytopathic effect. As illustrated in FIG. 13, while healthy HeLa cells not infected with the virus were seen in a control (Mock), a cytopathic effect was exhibited under a virus infected condition (Positive), showing cell shape changes, the formation of multi-nuclear cells (giant cells) (indicated by white arrows) and eventually cell death. Upon treatment with 8 μM of the NP of Example 1-1 under the same conditions, considerable inhibition of the PRV-induced formation of multi-nuclear cells was observed, and it was confirmed through these results that the nano-perforator of the present invention had an excellent anti-viral effect against a virus having an envelope even without a receptor.

The invention claimed is:

1. A method of treating a viral infection, the method comprising administering a pharmaceutically effective amount of an active ingredient of a nano-perforator comprising a lipid bilayer nanodisc, a membrane scaffold protein surrounding an outer circumferential surface of the nanodisc, and a receptor for a surface antigen of a virus to a subject having a viral infection, wherein the nano-perforator excludes a nano-perforator comprising 1-palmitoyl-2-oleoyl-sn-glycero-3 [phospho-rac-(1-glycerol)] (POPG) lacking the receptor for the surface antigen of the virus.

2. The method according to claim 1, wherein the nano-perforator perforates a lipid bilayer envelope of the virus.

3. The method according to claim 2, wherein the virus comprises one or more viruses of the family Bunyaviridae, the family Coronaviridae, the family Filoviridae, the family Flaviviridae, the family Hepadnaviridae, the family Orthomyxoviridea, the family Poxviridae, the family Rhabdoviridae, the family Retroviridae, the family Togaviridae, and the family Herpesviridae.

4. The method according to claim 2, wherein the active ingredient consists of the nano-perforator.

5. The method according to claim 1, wherein a lipid constituting the lipid bilayer nanodisc is a phospholipid.

6. The method according to claim 1, wherein the membrane scaffold protein is an amphipathic protein having a helix structure.

7. The method according to claim 1, wherein the surface antigen comprises one or more of hemagglutinin (HA) and-neuraminidase (NA).

8. The method according to claim 1, wherein the receptor comprises one or more of a sialic acid-containing glycolipid and a sialic acid-containing glycoprotein.

9. The method according to claim 8, wherein the sialic acid-containing glycolipid comprises one or more of a ganglioside and polysialic acid.

10. The method according to claim 1, wherein a molar ratio of (i) a sum of a lipid included in the lipid bilayer nanodisc and the receptor for the surface antigen of the virus to (ii) the membrane scaffold protein ranges from 10:1 to 800:1.

* * * * *